United States Patent
MacMillan et al.

(10) Patent No.: US 9,393,057 B2
(45) Date of Patent: Jul. 19, 2016

(54) SURGICAL SYSTEM AND METHOD

(71) Applicant: Pioneer Surgical Technology, Inc., Marquette, MI (US)

(72) Inventors: Adam MacMillan, Quincy, MA (US); Richard Nussbaum, Santa Clarita, CA (US)

(73) Assignee: PIONEER SURGICAL TECHNOLOGY, INC., Marquette, MI (US)

(*) Notice: Subject to any disclaimer, the term of this patent is extended or adjusted under 35 U.S.C. 154(b) by 0 days.

(21) Appl. No.: 14/504,512

(22) Filed: Oct. 2, 2014

(65) Prior Publication Data
US 2015/0141964 A1 May 21, 2015

Related U.S. Application Data

(60) Provisional application No. 61/888,443, filed on Oct. 8, 2013.

(51) Int. Cl.
*A61B 17/70* (2006.01)
*A61B 17/16* (2006.01)
(Continued)

(52) U.S. Cl.
CPC .......... *A61B 17/7094* (2013.01); *A61B 17/025* (2013.01); *A61B 17/1659* (2013.01);
(Continued)

(58) Field of Classification Search
CPC .......... A61B 17/7094; A61B 17/1659; A61B 17/28; A61B 17/02; A61B 17/3423; A61B 17/1757; A61B 17/707; A61B 17/8833; A61B 17/7097; A61B 17/8811; A61B 2017/90; A61B 17/025; A61B 17/3421; A61B 17/0206; A61B 2017/0256

USPC .................. 623/17.11; 606/79; 604/57, 518
See application file for complete search history.

(56) References Cited

U.S. PATENT DOCUMENTS 5,015,255 A    5/1991  Kuslich
5,489,307 A *  2/1996  Kuslich .............. A61B 17/1757
                                                    128/898

(Continued)

FOREIGN PATENT DOCUMENTS

WO          95/31948       11/1995

OTHER PUBLICATIONS

Apatech, "Silicate substituted synthetic bone graft", ApaTech Limited, 2 pages (May 2008).

(Continued)

*Primary Examiner* — Manuel Mendez
(74) *Attorney, Agent, or Firm* — Fitch, Even, Tabin & Flannery LLP

(57) ABSTRACT

In accordance with one aspect, an instrument is provided that permits the precise delivery of bone fusion material, such as autograft or allograft material, to one or more bones during surgical procedures. In another aspect, a system and a method are also provided for percutaneous delivery of bone fusion material, such as morselized autograft or bone graft, in a minimally invasive approach through one or more relatively small incisions in a patient. In yet another aspect, an expansion device is provided having an internal compartment and being shiftable between an insertion configuration and an expanded configuration. Bone fusion material may be injected into the internal compartment of the expansion device and travel therealong for bonding to one or more bones approximate the expansion device.

21 Claims, 45 Drawing Sheets

(51) Int. Cl.
  *A61B 17/17* (2006.01)
  *A61B 17/02* (2006.01)
  *A61B 17/88* (2006.01)
  *A61B 17/34* (2006.01)

(52) U.S. Cl.
  CPC ........... *A61B17/1757* (2013.01); *A61B 17/707* (2013.01); *A61B 17/0206* (2013.01); *A61B 17/3421* (2013.01); *A61B 17/7097* (2013.01); *A61B 17/8811* (2013.01); *A61B 17/8833* (2013.01); *A61B 2017/0256* (2013.01)

(56) References Cited

U.S. PATENT DOCUMENTS

| | | | |
|---|---|---|---|
| 5,549,679 A | 8/1996 | Kuslich | |
| 5,571,189 A | 11/1996 | Kuslich | |
| 5,741,261 A * | 4/1998 | Moskovitz | A61B 17/02 606/279 |
| 5,928,239 A * | 7/1999 | Mirza | A61B 17/1668 606/167 |
| 5,954,671 A | 9/1999 | O'Neil | |
| 6,383,188 B2 | 5/2002 | Kuslich et al. | |
| 6,620,169 B1 | 9/2003 | Peterson et al. | |
| 6,712,853 B2 | 3/2004 | Kuslich | |
| 7,025,771 B2 | 4/2006 | Kuslich et al. | |
| 7,056,345 B2 | 6/2006 | Kuslich | |
| 7,220,282 B2 | 5/2007 | Kuslich | |
| 2008/0033575 A1 * | 2/2008 | Walsh | A61F 2/441 623/23.72 |
| 2009/0312764 A1 | 12/2009 | Marino | |
| 2012/0197399 A1 * | 8/2012 | Kirschman | A61B 17/7059 623/17.11 |
| 2013/0253591 A1 | 9/2013 | Kornel | |

OTHER PUBLICATIONS

Actifuse MIS System, "Spinal/Orthopedic Applications", ApaTech Limited, 2 pages (Oct. 8, 2009).
Actifuse MIS System, "Bone Graft Substitute Silicate Substituted Calcium Phosphate", Baxter, 4 pages (Sep. 2010).
Quickdraw Bone Harvester, "Minimally-Invasive Autografting System", Paradigm BioDevices, 2 pages (Mar. 2012).
Osteobiologics, "Symphony Graft Delivery System|GDS", DePuySpine, 4 pages (2001).
Osteobiologics, Stryker, 2 pages (2011).
OptiMesh 1500E, "Percutaneous Interbody Fusion Surgical Technique", Spineology, 15 pages (Feb. 2010).
Actifuse MIS System, "Bone Graft Substitute", 1 page (May 2008).

* cited by examiner

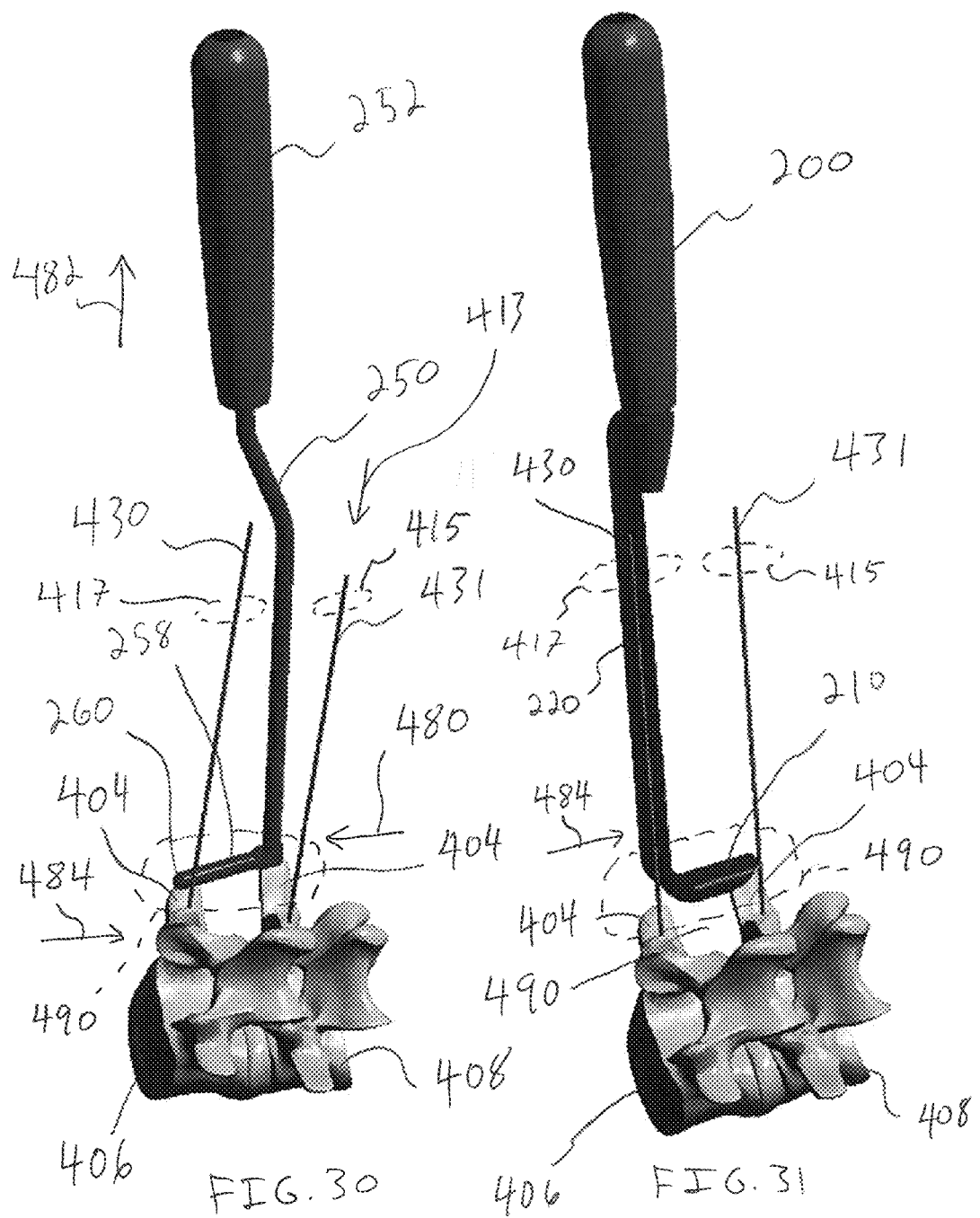

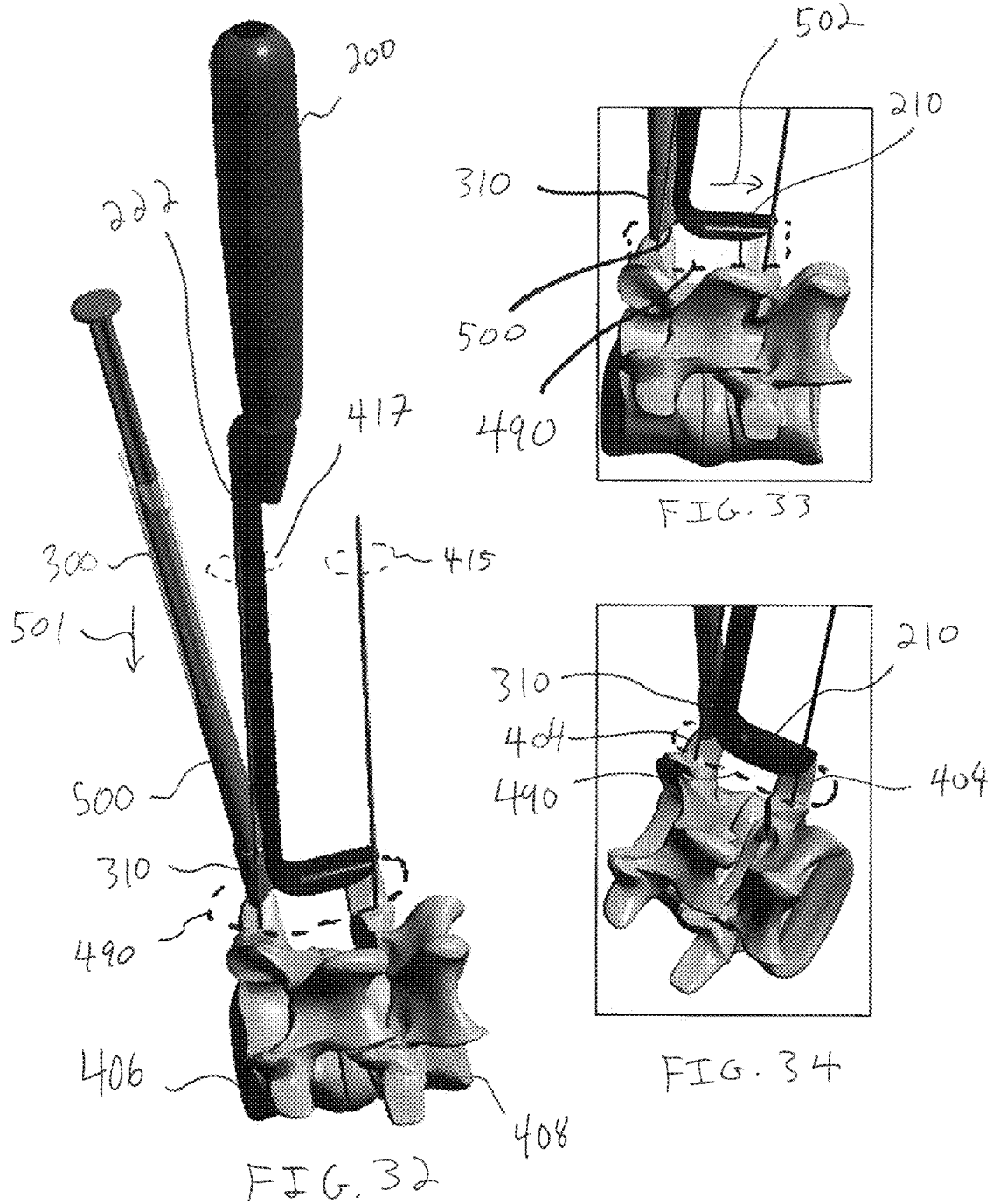

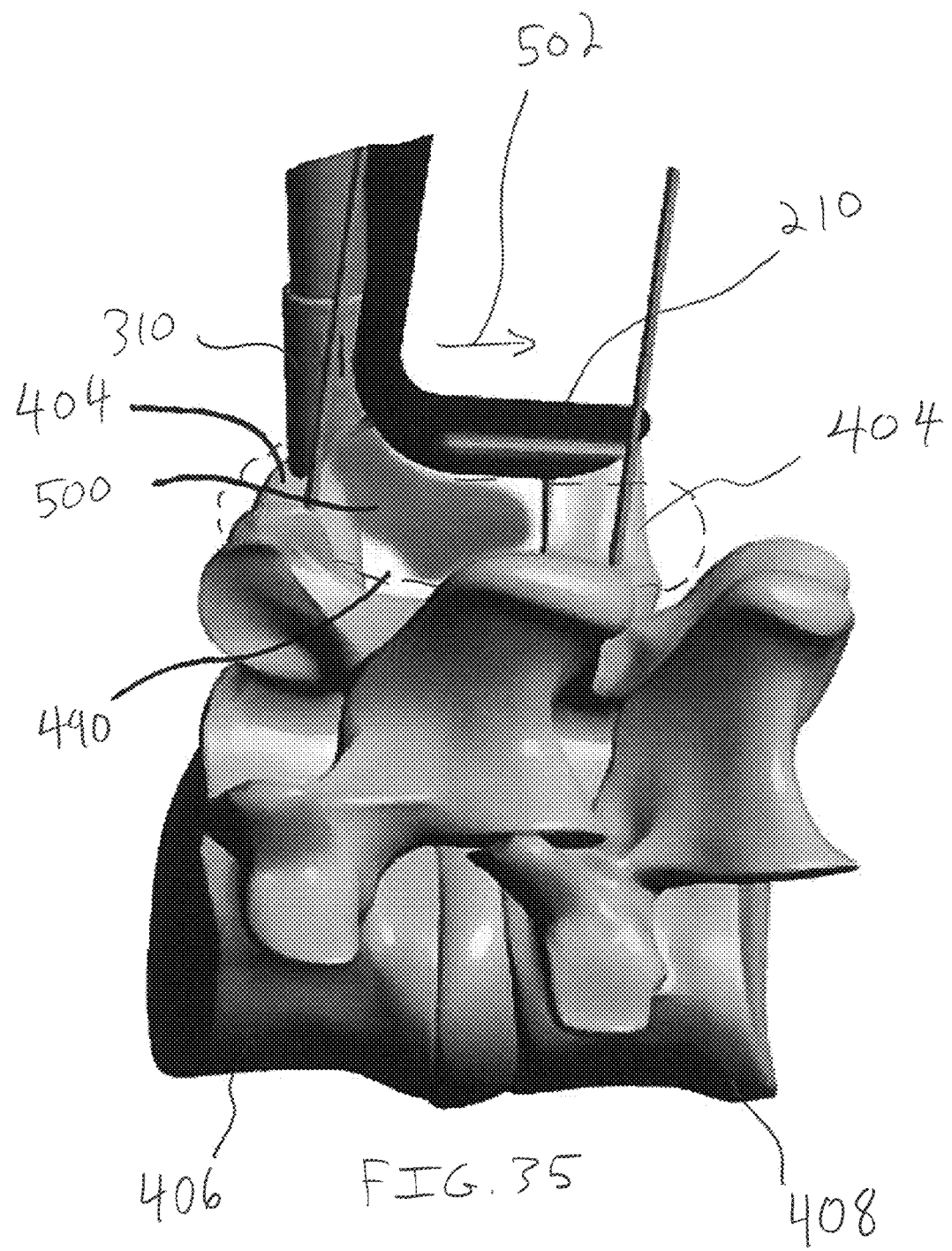

SURGICAL SYSTEM AND METHOD

CROSS-REFERENCE TO RELATED APPLICATION

This application claims the benefit of U.S. Provisional Patent Application No. 61/888,443, filed Oct. 8, 2013, which is hereby incorporated herein by reference in its entirety.

FIELD OF THE INVENTION

The invention relates to surgical operations and, more specifically, to surgical operations for stabilizing one or more bones.

BACKGROUND

Surgical techniques for stabilizing bones, such as vertebra, are known. In some approaches, bone screw assemblies are driven into pedicles of two or more vertebrae and a spinal rod is placed within yokes of the bone screw assemblies and secured therewith. The bone screw assemblies and spinal rod stabilize the vertebrae in conjunction with one or more implants positioned in the intervertebral disc space. To further stabilize the vertebrae, a column of bone graft material can be placed in the posterolateral gutter of each vertebrae between the spinous process and transverse process of the vertebra. The column of bone graft material is oriented to extend generally parallel to the spinal rod and bonded to the transverse processes of the vertebrae. This procedure may be referred to as a posterolateral fusion (PLF). The bone graft material encourages bone growth into and along the column which produces a rigid, boney structure spanning the vertebrae and providing additional support against relative movement of the vertebrae. Traditionally, access to the vertebrae is obtained using a "full open" procedure that involves making a long incision parallel to the patient's spine and retracting tissues surrounding the vertebrae. The full open approach may not be desirable in some instances, where the long incision may increase tissue trauma and patient recovery time.

BRIEF DESCRIPTION OF THE DRAWINGS

FIGS. 22-36 are views showing a process of implanting a bone fusion substance on a pair of vertebrae;

DETAILED DESCRIPTION OF THE PREFERRED EMBODIMENTS

Figure 1:
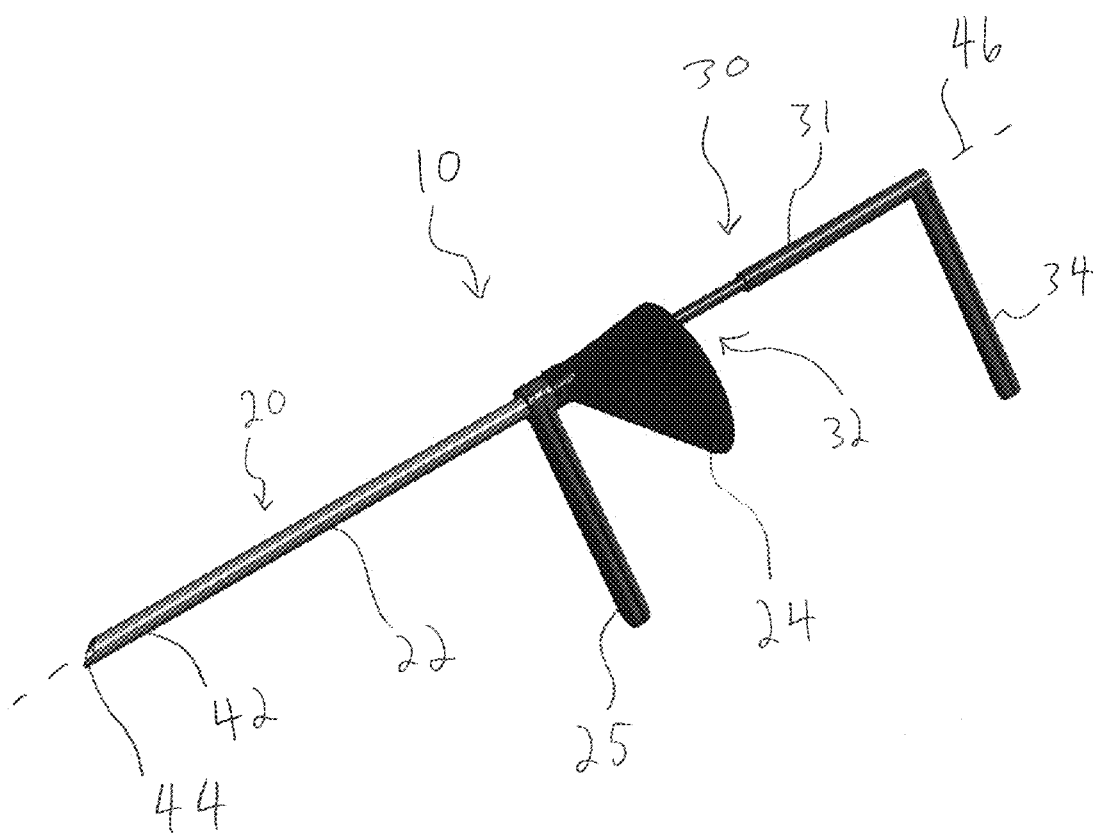
FIG. 1 is a perspective view of a delivery instrument having a guide for holding a bone fusion substance and a driver for driving the substance outward from the guide.

In FIG. 1, a delivery instrument 10 is shown for use in the delivery of bone fusion material, such as autograft and allograft materials, in surgical procedures. The delivery instrument 10 permits precise placement of the bone fusion material 12 on one or more bones during a variety of surgical procedures, including bilateral posterolateral fusion (see FIG. 6) and intervertebral operations involving implants 14 (see FIG. 11).

With reference to FIG. 1, the instrument 10 has a guide 20 with a shaft 22 and a funnel 24 connected to the shaft 22. The funnel 24 receives bone fusion material 12 to be directed into the guide shaft 22 and injected into a surgical site. The instrument 10 also has a driver 30 with a distal end 32 (see FIG. 8) sized to fit within the guide shaft 22 and drive the bone fusion material 12 out from the guide shaft 22. The guide 20 has a handle 25 for maneuvering the shaft 22 which permits a user to direct bone fusion material 12 flow by turning the handle about a longitudinal axis 46 of the instrument 10, as discussed in greater detail below. The driver 30 also has a handle 34 for being grasped to advance the driver 30 along the instrument longitudinal axis 46.

To deliver the bone fusion material 12, the bone fusion material 12 is initially loaded into the funnel 24 and advanced into the shaft 22 such as by packing the material into the guide shaft 22. Next, the distal end 32 of the driver 30 is advanced into the funnel 24 and into the shaft 22. Once the guide shaft tip 42 has been positioned at a desired location in the patient, the driver handle 34 is moved toward the guide handle 25 in direction 40 which causes the driver distal end 32 to drive bone fusion material 12 distal from the opening 44 at the guide shaft tip 42 and into the patient, as shown in FIGS. 1-2.

Figure 2:
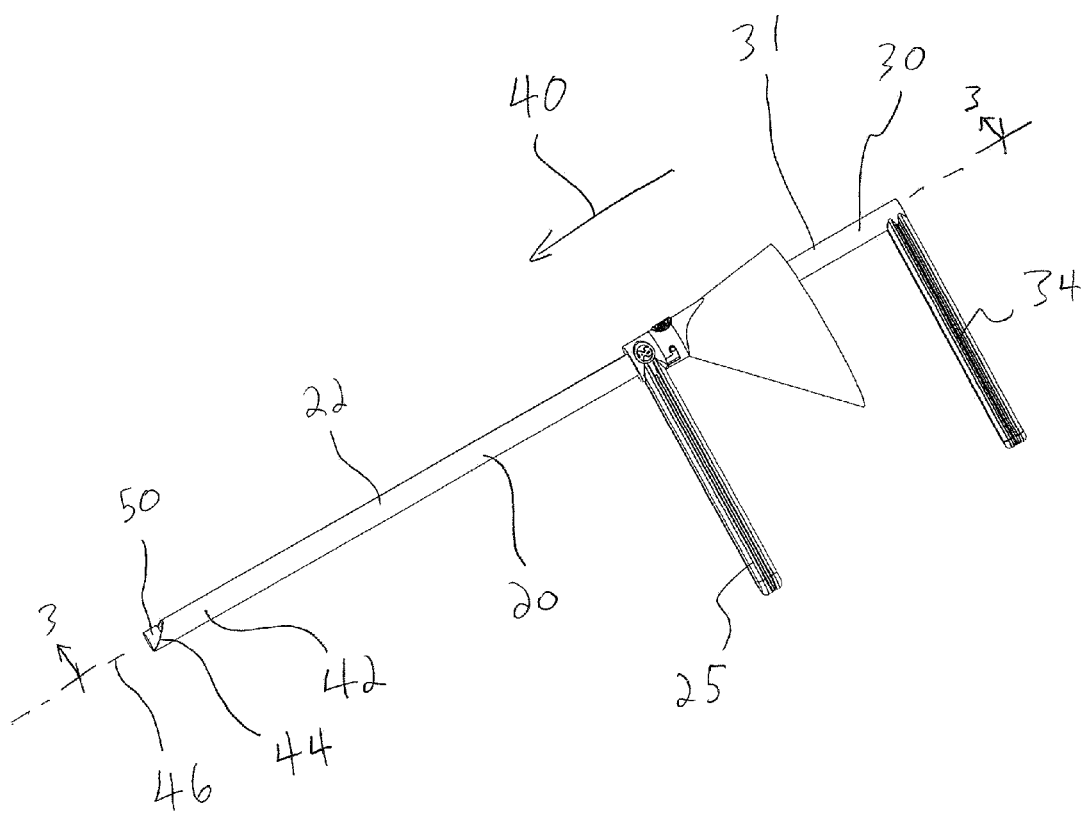
FIG. 2 is a perspective view similar to FIG. 1 showing the driver shifted forwardly within the guide such that a plunger of the driver extends outwardly from a tip of the guide.
Figure 3:
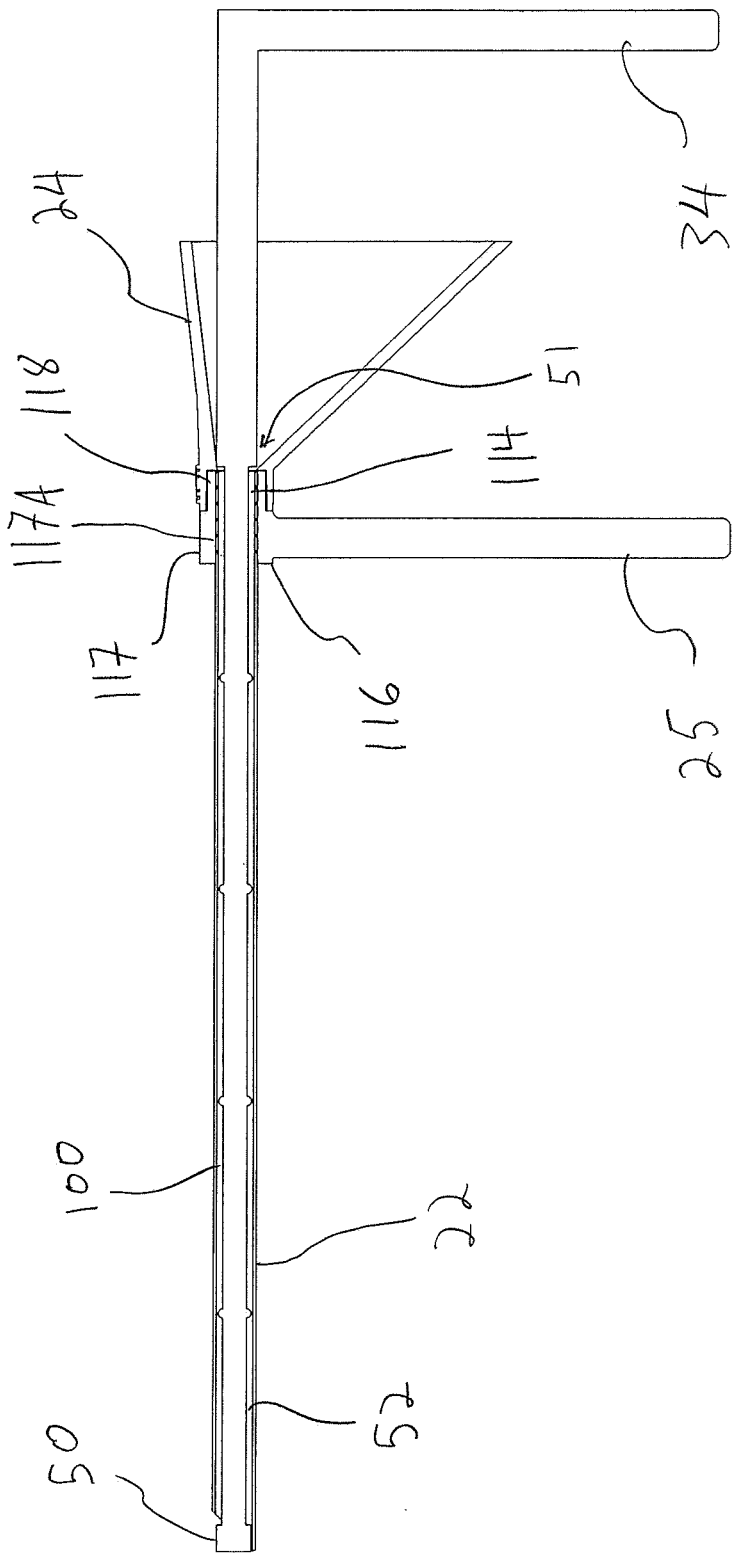
FIG. 3 is a cross-sectional view taken across line 3-3 in FIG. 2 showing a shaft of the driver received in a shaft of the guide.
Figure 4:
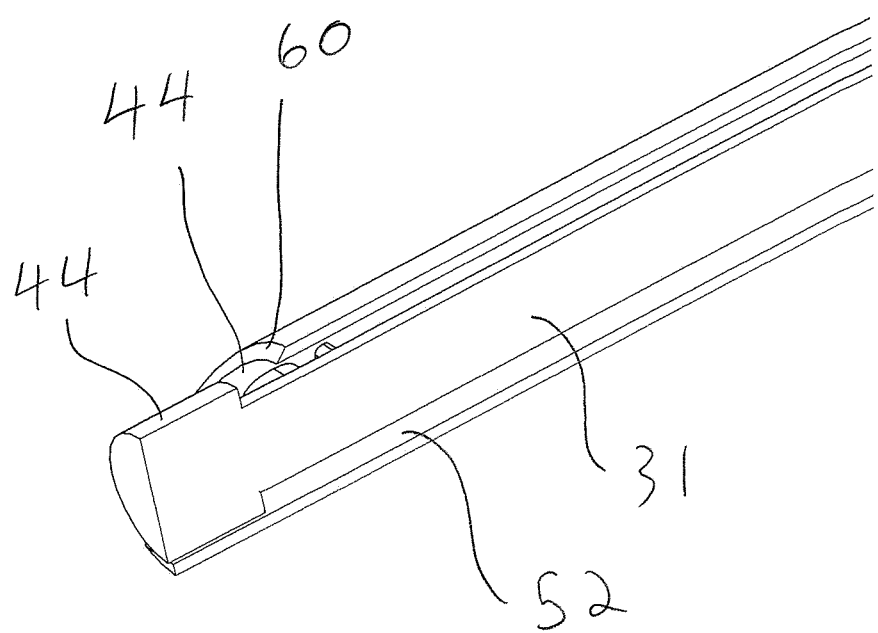
FIG. 4 is an enlarged cross-sectional view of the instrument of FIG. 1 showing a plunger of the driver extending outwardly from an opening of the guide shaft.

With reference to FIGS. 2 and 3, the distal tip 42 of the guide 20 has a tapered opening 44 configured to direct bone fusion material 12 in a direction transverse to the longitudinal axis 46 of the instrument 10, as discussed in greater detail below. The driver distal end portion 32 includes a plunger 50 configured to engage and substantially seal against an inner surface 52 (see FIG. 3) of the guide shaft 22 as the driver 30 is advanced in the distal direction 40. The tight seal of the plunger 50 against the guide shaft inner surface 52 ensures that substantially all of the bone fusion material 12 in the guide shaft 22 distal of the plunger 50 is driven outward with distal movement of the guide 30. With reference to FIG. 2, continued advancement of the driver 30 in direction 40 causes the plunger 50 to partially exit the guide tip opening 44, which permits the plunger 50 to fully empty the guide shaft 22 without extending axially fully beyond the tip 42 of the guide 20 for limiting contact of the plunger 50 and surrounding tissue and thereby avoiding irritation to the tissue. In one form, the instrument 10 includes a stop 51 (see FIG. 3) which limits axial movement of the driver 30 into the guide 20.

Figure 5:
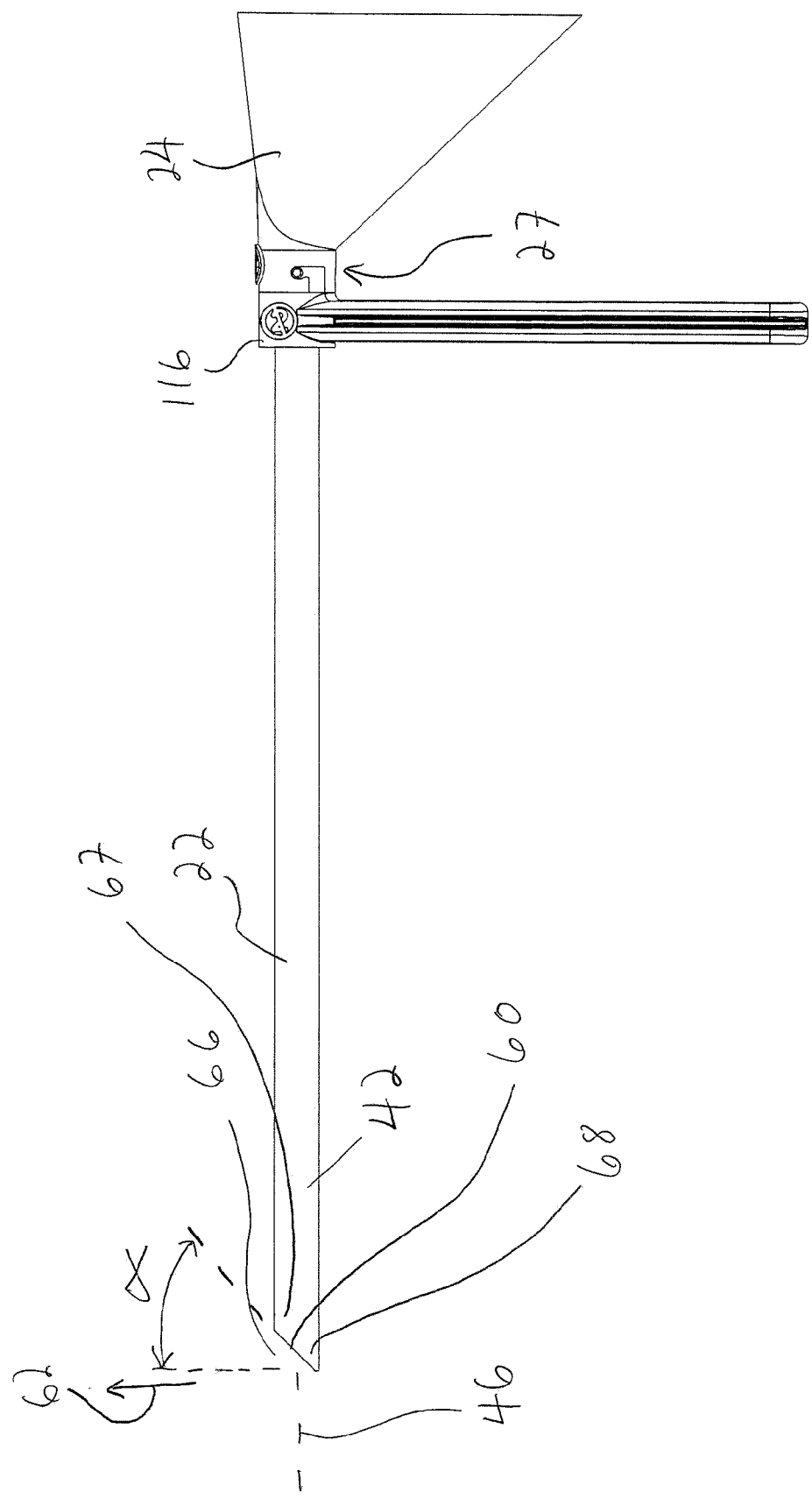
FIG. 5 is a side elevational view of the guide of FIG. 1 showing an angled tip of the guide shaft.
Figure 6:
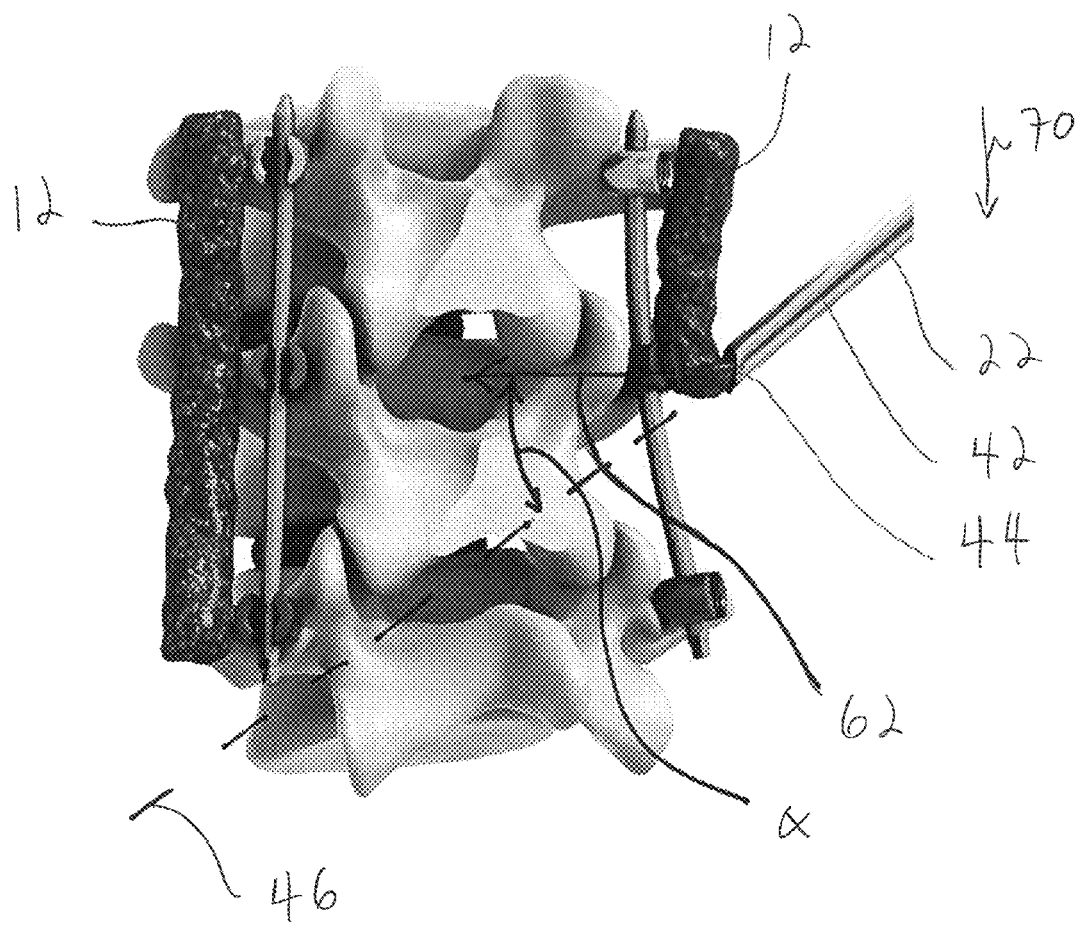
FIG. 6 is a schematic view of the tip of the instrument of FIG. 1 showing the instrument being used to discharge the bone fusion substance in a direction transverse to a longitudinal axis of the guide shaft.

With reference to FIGS. 5 and 6, the tip 42 of the guide 20 includes a chamfered edge 60 that defines the opening 44 with the edge 60 oriented to extend at an angle α relative to the shaft longitudinal axis 46. In one form, the angle α is approximately forty-five degrees. Because the edge 60 extends at an angle relative to the longitudinal axis 42, the bone fusion material 12 will tend to shift laterally in direction 62 as the graft 12 travels out from the tip 42. More specifically, the bone fusion material 12 expands laterally upon reaching region 66 toward one side 67 of the shaft 22. However, the bone fusion material 12 toward the opposite side 68 of the shaft 22 is at the same longitudinal position along the shaft 22 but is still surrounded by the shaft 22 and is thereby restricted from expanding laterally. By generally directing the bone fusion material in transverse direction 62 (see FIG. 6), the instrument 10 permits a user to quickly and easily place a column of bone fusion material 12 along one or more bones by moving the instrument 10 in direction 70 while exerting a longitudinal drive force on the material 12 for driving the bone fusion material 12 from the guide shaft 20.

Figure 7:
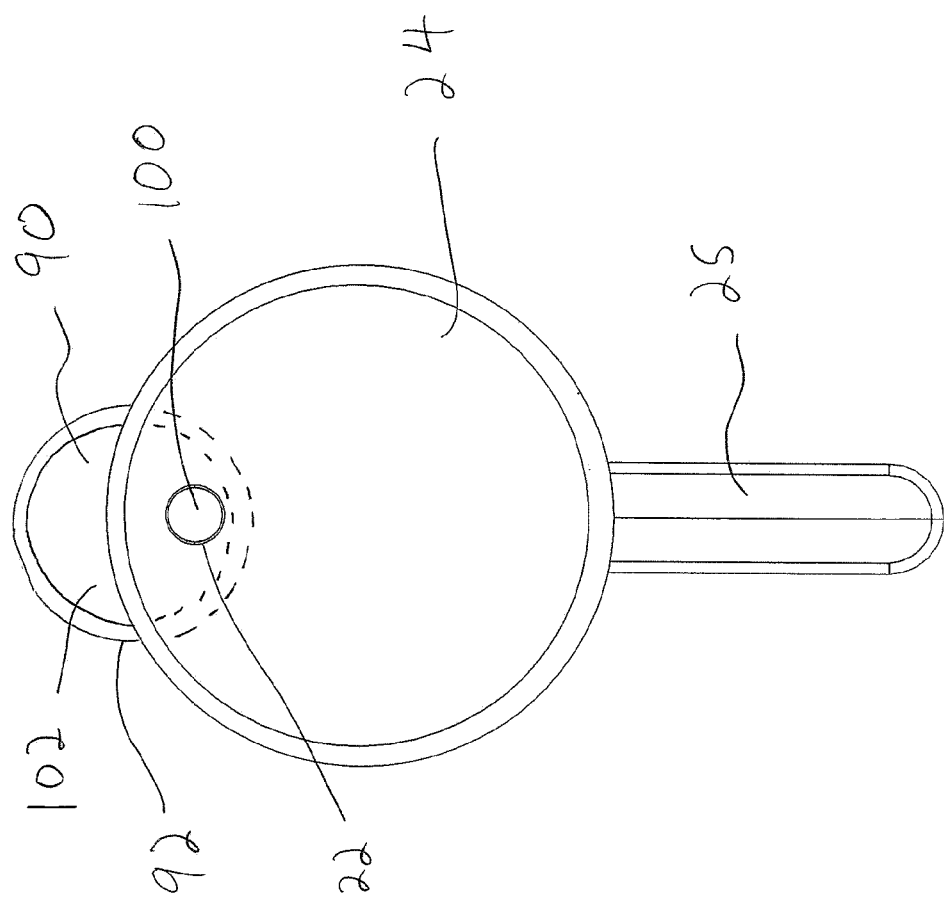
FIG. 7 is a rear plan view of the guide of FIG. 1 with the shaft of the guide received in a through opening of a tubular working channel and showing the offset funnel of the guide permitting viewing around the offset funnel and down a portion of the tubular working channel.

Another advantage of the delivery instrument 10 is that the funnel 24 is laterally offset relative to the instrument longitudinal axis 46 which reduces visual obstruction by the funnel 24 when the guide 20 is positioned in a surgical working channel, as shown in FIG. 7. More specifically, the guide shaft 22 may be advanced into a through opening 90 of a tubular working channel 92 to position the guide tip 42 near the surgical site. The guide shaft 22 defines a cannula 100 sized to receive the driver shaft 31 and extends between the tip 42 and the funnel 24. As shown in FIG. 7, the guide shaft 22 and the cannula 100 thereof are located at one side of the tubular working channel through opening 90 while a portion 102 of the through opening 90 remains unobstructed. In this manner, the surgeon may maintain a visual line of sight to the surgical site while loading bone fusion material 12 into the funnel 24 and/or may advance tools into the unobstructed portion 102 of the through opening 90 without having to withdraw the guide shaft 22 from the through opening 90.

Figure 8:
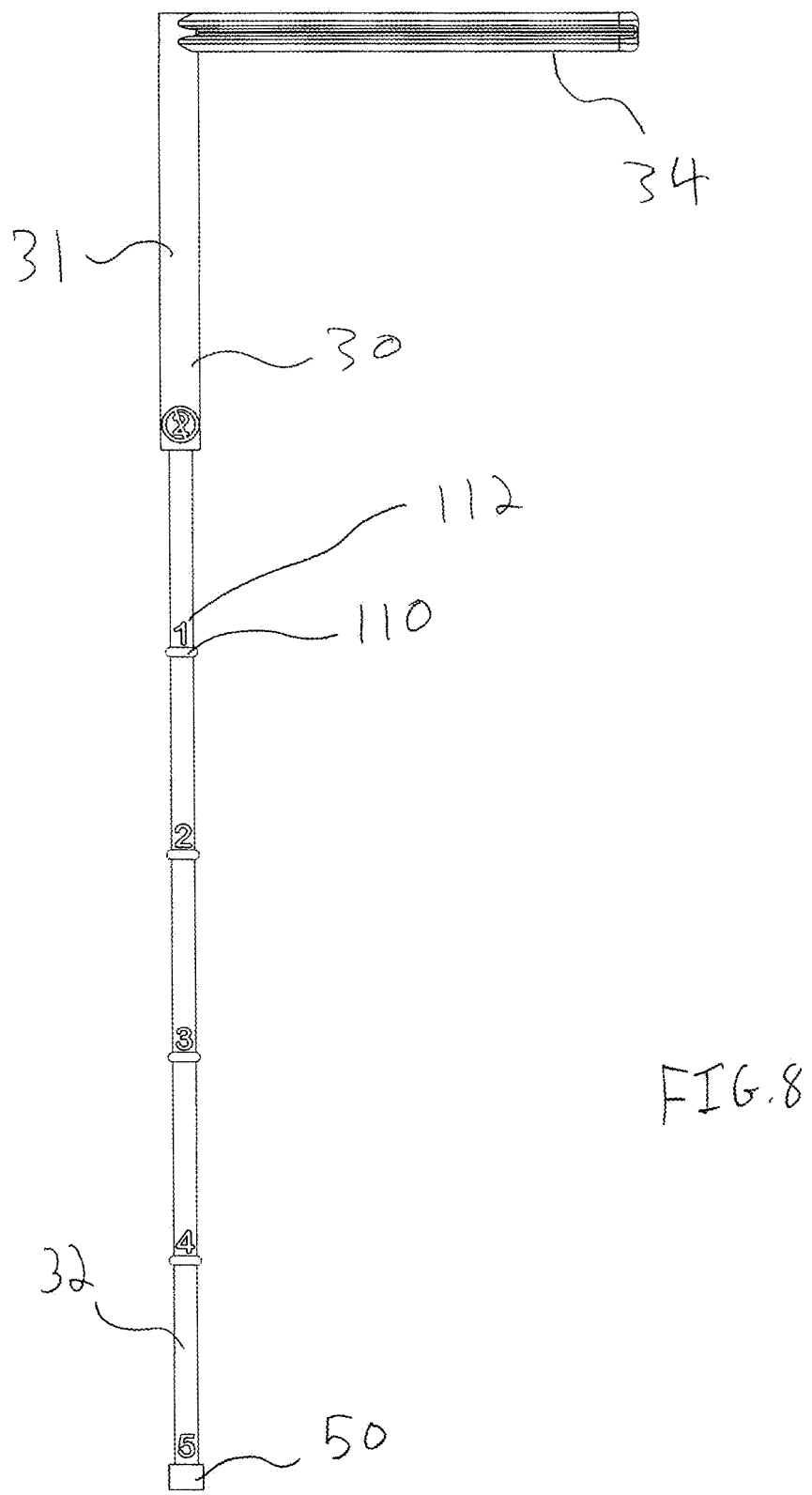
FIG. 8 is a side elevational view of the driver of FIG. 1 showing a graduated shaft of the driver.

With reference to FIG. 8, the driver 30 may be a graduated driver that permits a surgeon to visually determine the volume of bone fusion material 12 discharged from the instrument by visually observing the longitudinal position of the driver 30 within the guide 20. The driver shaft 31 may have ribs 110 positioned at predetermined longitudinal increments along the shaft 31 and indicia 112 positioned at the ribs 110. The indicia 112 can be numbers, letters, or other symbols that may be used to aid the surgeon and placement of the bone fusion material 12.

For example, the guide shaft 22 may have a length of about 165 mm and an internal volume of approximately 5 cubic centimeters of bone fusion material 12. Once the guide shaft 22 has been filled with bone fusion material 12 (i.e., the guide shaft 22 contains 5 cubic centimeters of bone graft material), a user can advance the driver distal end 32 into the funnel 24 and into a proximal end 114 (see FIG. 3) of the guide shaft 22. At this point, the indicia "5" will be located just outside of the guide shaft 22 proximal end 114. The user then advances the driver distal end 32 farther into the guide shaft cannula until the indicia "4" is located just outside of the guide shaft proximal end 114. By visually observing that the driver 30 has advanced longitudinally one increment, the user knows that one cubic centimeter of bone fusion material 12 has been discharged from the guide shaft distal end 42. This permits a precise placement of a desired amount of bone fusion material 12 simply by advancing the driver 30 within the guide 20.

Figure 9:
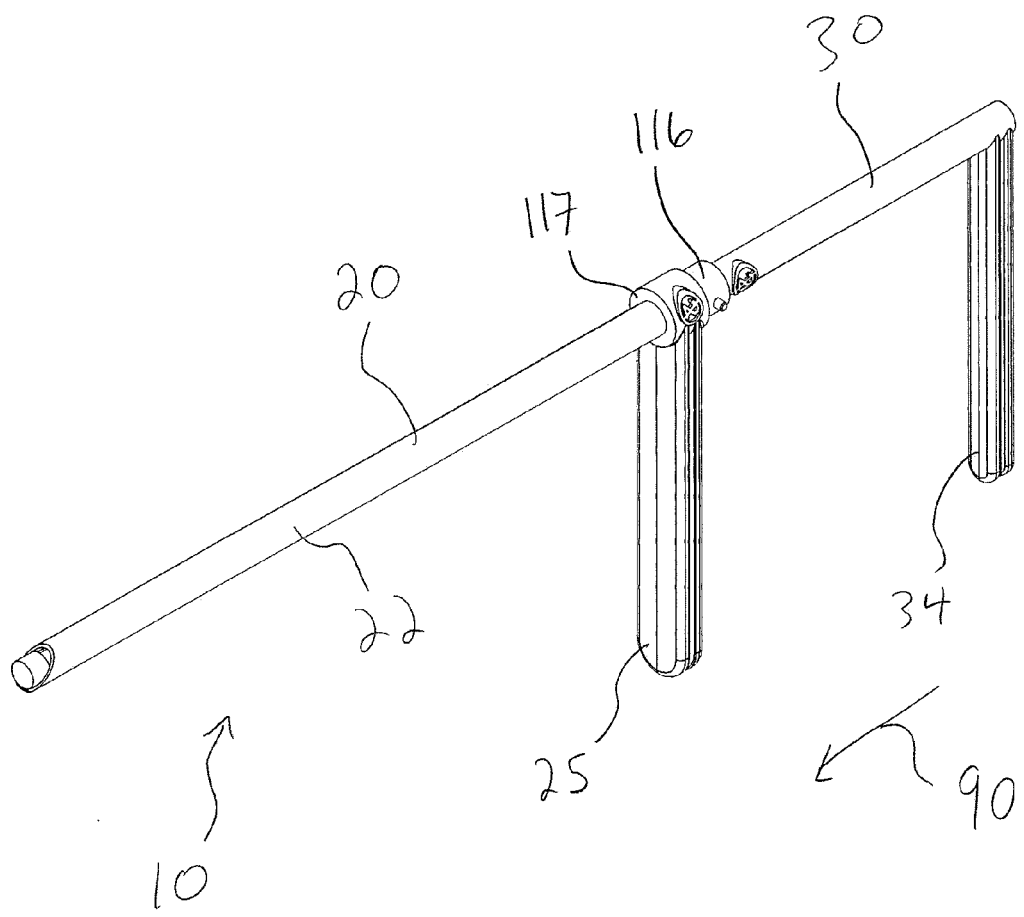
FIG. 9 is a perspective view of the instrument of FIG. 1 with the funnel removed.

With reference to FIGS. 3 and 9, the handle 25 of the guide 20 includes a fitting 116 having a sleeve 117 with a through opening 117A sized to receive the guide shaft 22, which is fixedly mounted in the sleeve 117 such as by use of an adhesive or a fastener. The guide fitting 116 also has a collar 118 to which the funnel 24 is releasably mounted. In one form, the fitting collar 118 and the funnel 24 have a bayonet connection 27 therebetween (see FIG. 5). The releasable funnel 24 permits the guide 20 and the driver 30 to be used without the funnel 24 obstructing viewing of the patient, as shown in FIG. 9.

Figure 10:
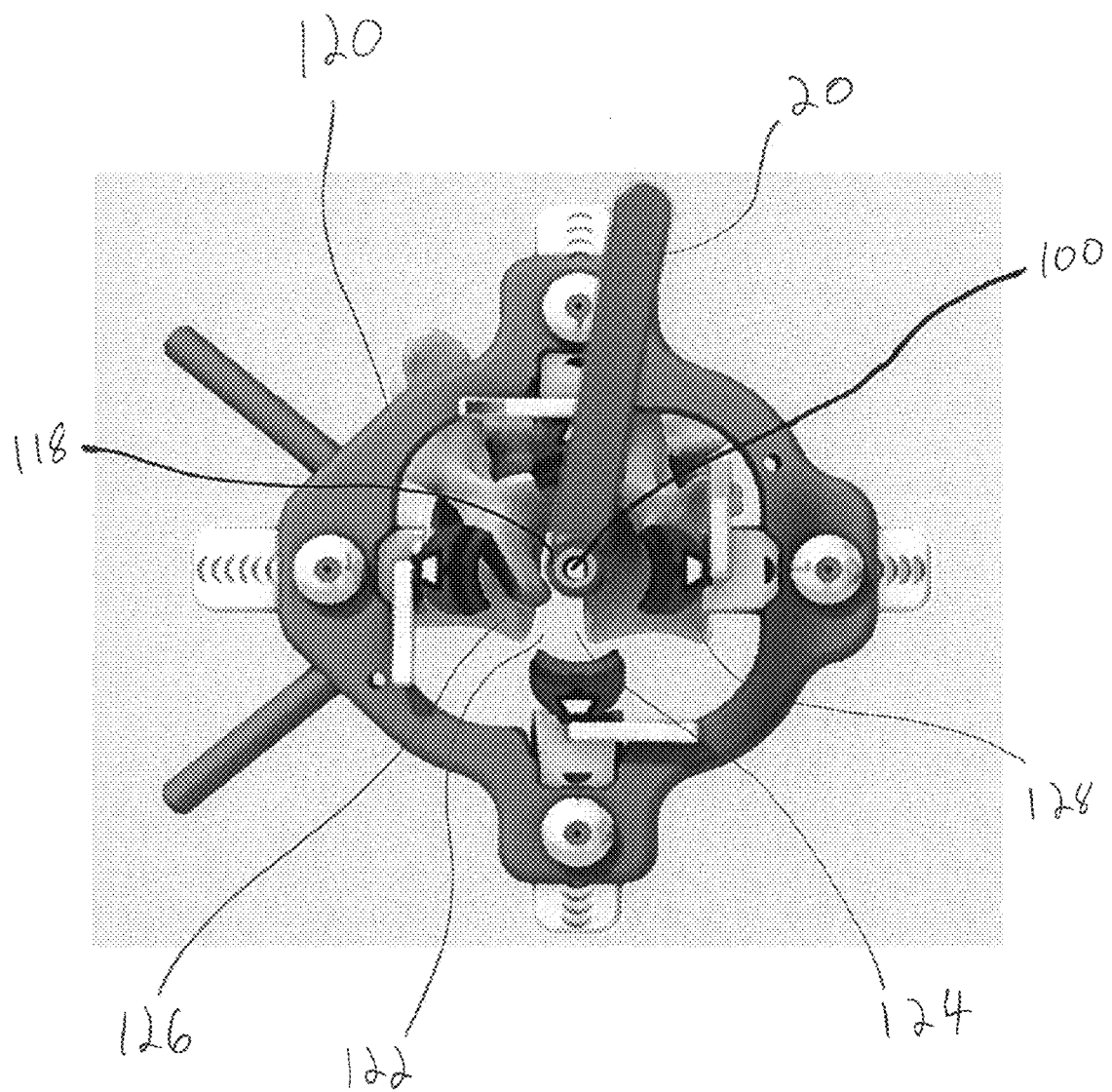
FIG. 10 is a rear plan view of the guide of FIG. 1 with the shaft of the guide inserted into a retracted working channel showing the cannula of the guide permitting viewing of an intervertebral space.

With reference to FIG. 10, another advantage of the instrument 10 is that the guide 20 can first be inserted into an incision or surgical working channel and the user can look through the cannula 100 to visually confirm that the bone fusion material 12 will be positioned in a desired location. Once the guide 20 is properly oriented and held in place such as by using an iron intern, the funnel 24 can be connected to the guide fitting collar 118, bone fusion material 12 can be loaded into the funnel 24 and guide cannula 100, and the driver 30 can be used to drive the bone fusion material into the surgical site as discussed above.

For example, a retractor 120 may be used to establish a working channel 122 into an intervertebral space 124 between vertebrae 126, 128 as shown in FIG. 10. The guide shaft tip 42 is advanced down the working channel 122 and positioned near the intervertebral space 124. At this point, the surgeon may look down the guide cannula 100 and observe a portion of the intervertebral space 124.

Figure 11:
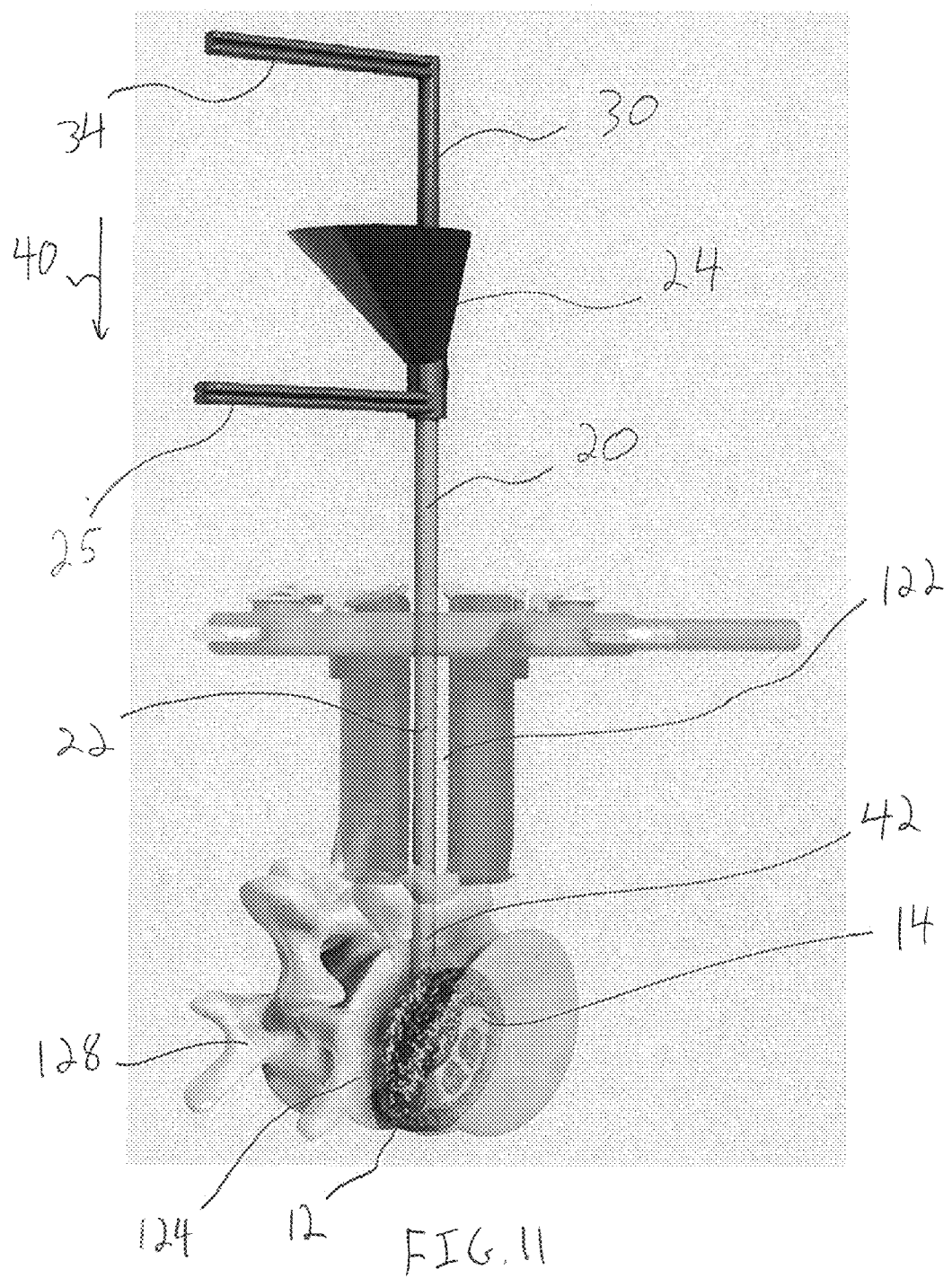
FIG. 11 is a perspective view of the instrument of FIG. 1 showing the shaft of the guide inserted in a retracted working channel and the driver being advanced to discharge graft material outward from the guide and into an intervertebral space about an implant.

Next, the funnel 24 may be connected to the guide fitting 118 and bone fusion material 12 loaded into the cannula 100 of the guide 20. The driver distal end 32 is advanced into the proximal end 114 of the guide shaft 22 and the driver handle 34 shifted in direction 40 toward the guide handle 25, as shown in FIG. 11. The movement of the driver distal end 32 along the guide cannula 100 forces the bone fusion material 12 out from the guide tip 42 and into the intervertebral space 124. The handle 25 may be turned, lifted, lowered, and/or pivoted to maneuver the guide shaft tip 42 as desired to discharge the bone fusion material 12 in and about the implant 14.

A system and method are also provided herein that facilitates the percutaneous delivery of measured amounts of bone fusion material, such as morselized autograft or bone graft, in a minimally invasive approach through one or more small incisions in a patient. The incisions may be 1-2 centimeters in length and be made in the patient to advance one or more tools therethrough for placement of the bone fusion material. Alternatively, the incisions can be incisions made for insertion of a fixation system, such as bone screw assemblies, into the patient. The system and method may be used in a variety of procedures, including delivery of bone graft to osteotomy sites, such as open osteotomies of the tibia and femur. Various aspects of the system and method could be used in other procedures, such as kyphoplasty procedures. One type of bone graft material that may be used with the following system and method is nanOss Bioactive Loaded®, from Pioneer Surgical Technology, Inc. of Marquette, Mich.

Figure 12:
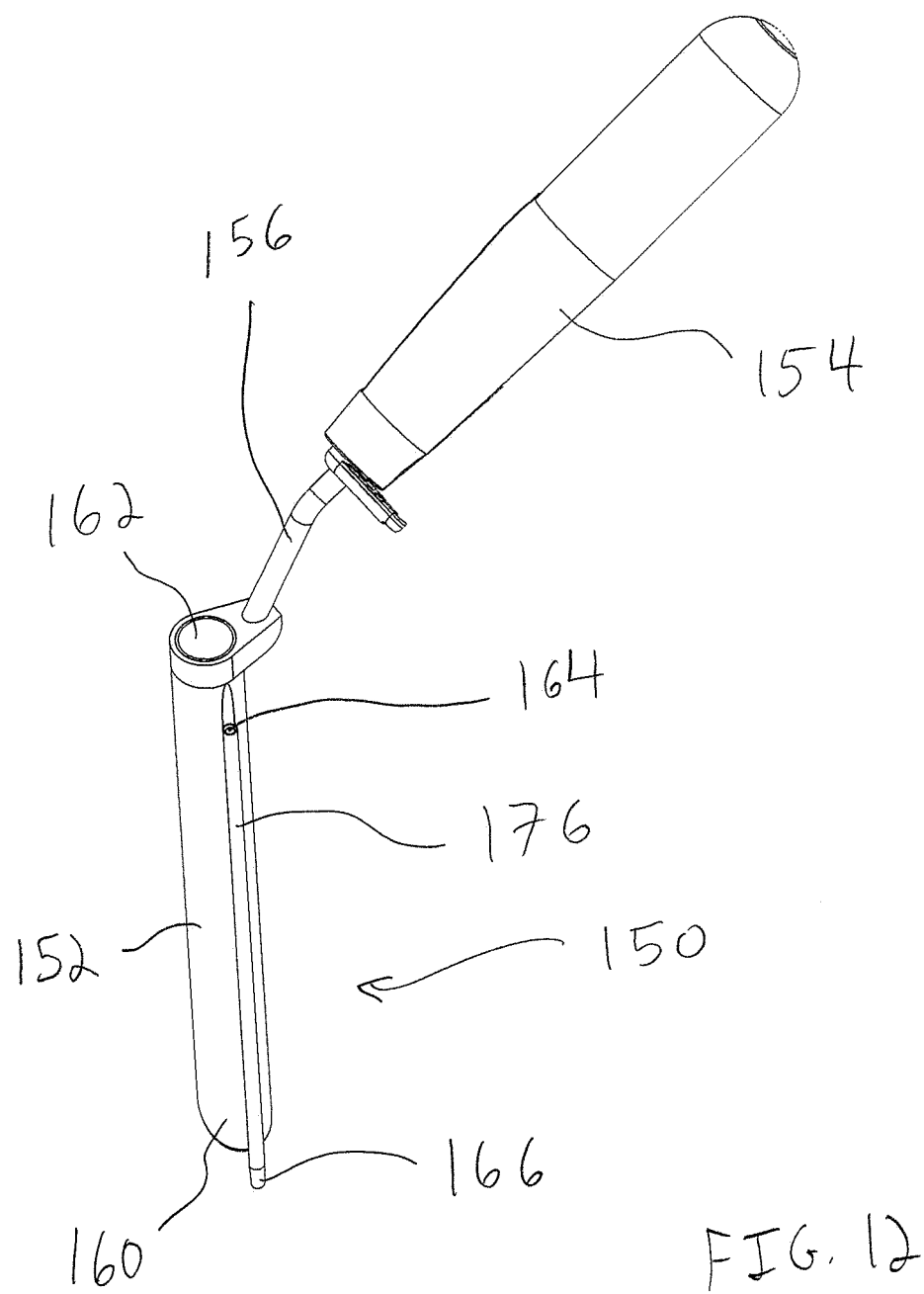
FIG. 12 is a perspective view of a guide tool showing primary and secondary bores of the guide tool.
Figure 13:
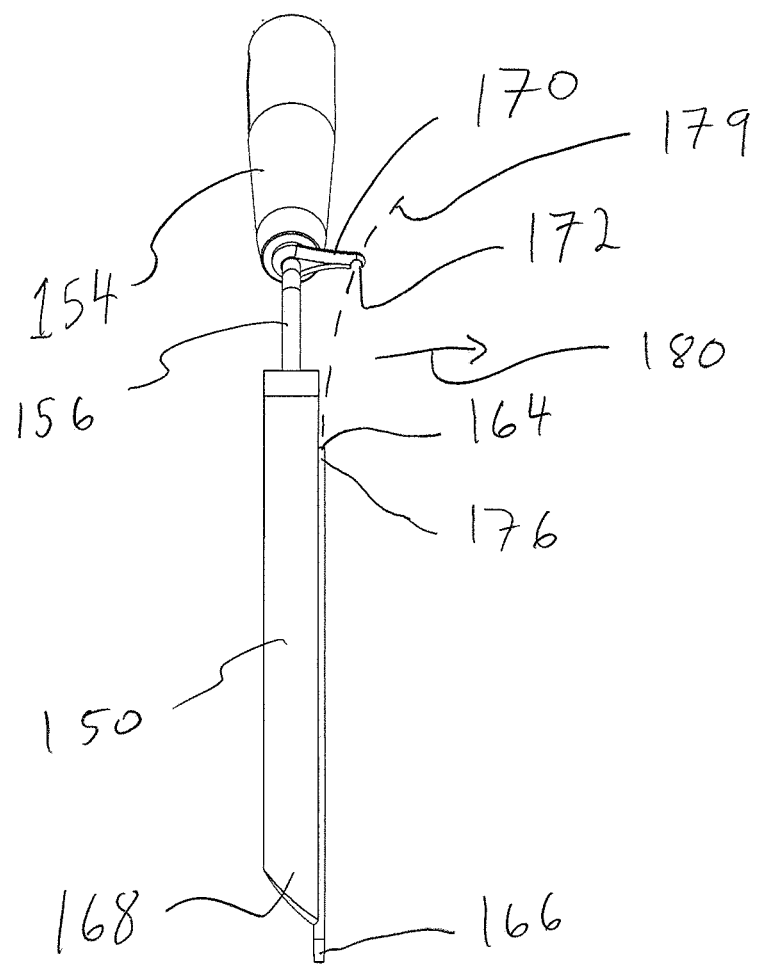
FIG. 13 is a front elevational view of the guide tool of FIG. 12 showing a tip of the tool extending beyond a body of the tool.
Figure 14:
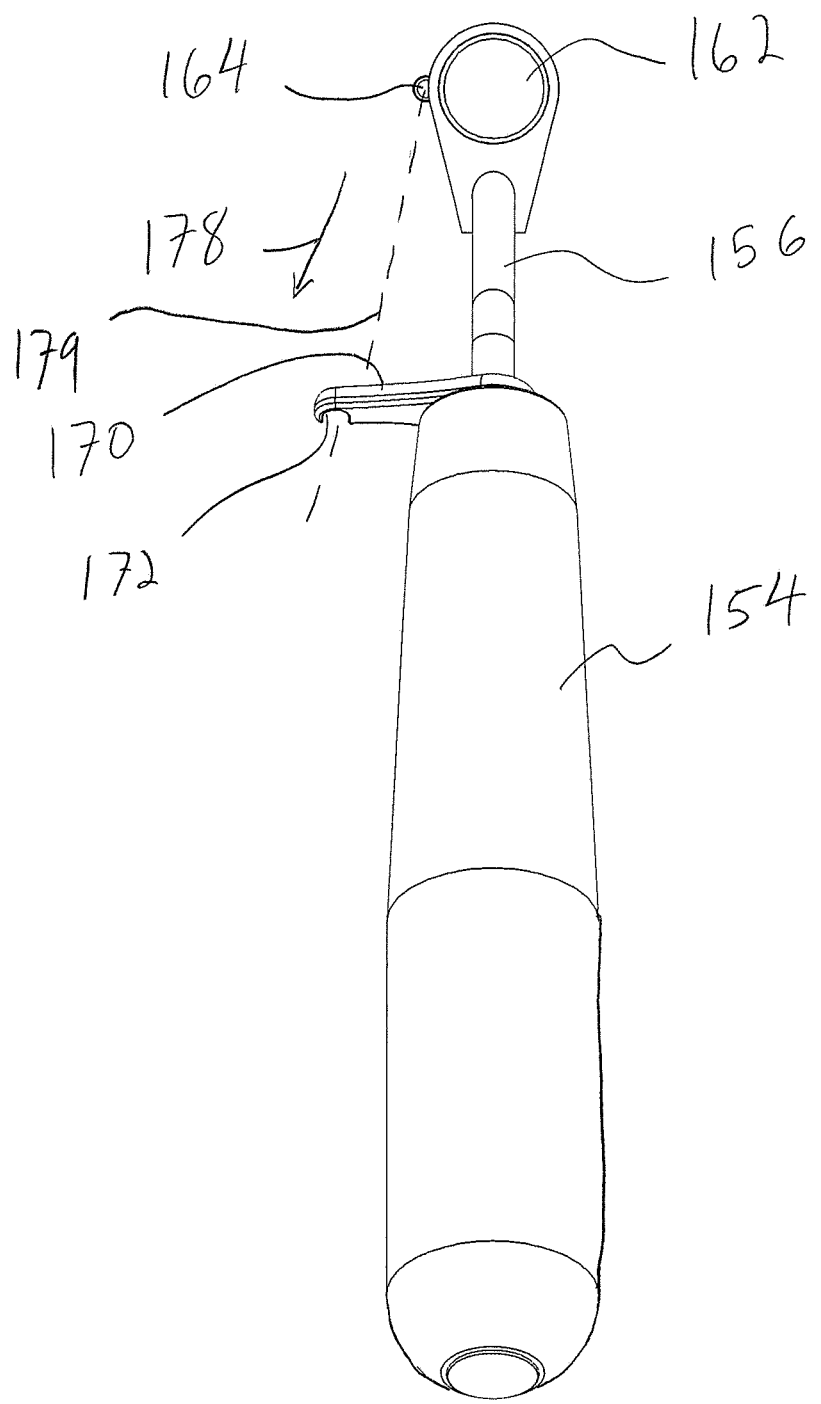
FIG. 14 is a top plan view of the guide tool of FIG. 12 showing the primary bore of the guide tool, the secondary bore, and a hook of the guide tool disposed proximally and laterally relative to the primary bore.

With reference to FIGS. 12-14, a guide tool 150 is provided for docking with a bone and guiding instruments to the bone. The guide tool 150 protects tissue from the instruments being guided through the guide tool 150 and directs, for example, the cutting tips of the instruments into the bone. The guide tool 150 has a body 152 sized to extend through a percutaneous incision and a handle 154 connected to the body 152 by a rod 156. The handle 154 permits the user to advance the body 152 into the incision and position a tip 160 of the body 152 near a desired location on the bone. The body 152 includes a primary bore 162 sized to receive instruments for preparing a surface of the bone, such as a burr, and a secondary bore 164 lateral to the primary bore 162 sized to receive a guide wire. The body 152 includes a tip 166 extending beyond a tapered end 168 of the body, as shown in FIG. 13. The tip 166 may be pointed at a distal end thereof to facilitate driving of the tip 166 into bone.

With reference to FIG. 13, the guide tool 150 includes a hook 170 extending laterally relative to the handle 154 with an opening 172 sized to receive a guide wire 179, shown in dashed in FIGS. 13 and 14, extending outward from the secondary bore 164. The hook 170 positions the guide wire 179 laterally away from the primary bore 162 and any tools which may be advanced through the primary bore 162 to avoid interference therewith. More specifically and with reference to FIG. 14, the secondary bore 164 is disposed laterally relative to the primary bore 162. The guide tool 150 and secondary bore 164 thereof may be advanced along the guide wire 179 until the guide wire 179 advances out from a proximal end 176 (see FIG. 13) of the secondary bore 164. The end of the guide wire 179 extending out from the secondary bore proximal end 176 may be bent laterally in direction 180 away from rod 156 and toward the recess 172 of the hook 170, as shown in FIG. 13. The guide wire 179 is then placed into the hook recess 172 and out of the way of the user, as shown in FIG. 14.

Figure 15:
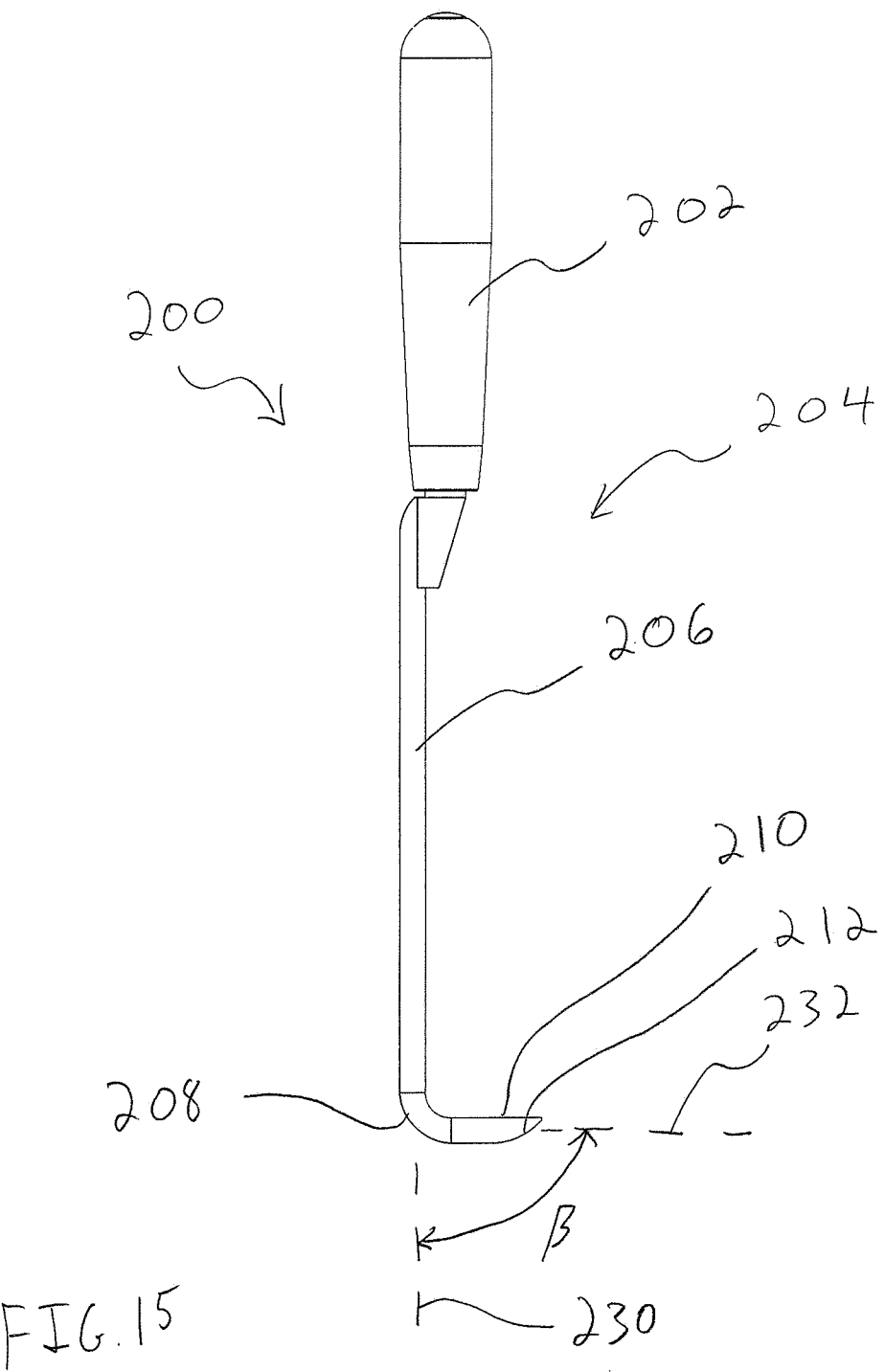
FIG. 15 is a side elevational view of a bone fusion material guide showing a shaft and an tip of the bone fusion material guide with the tip extending at an angle to shaft.
Figure 16:
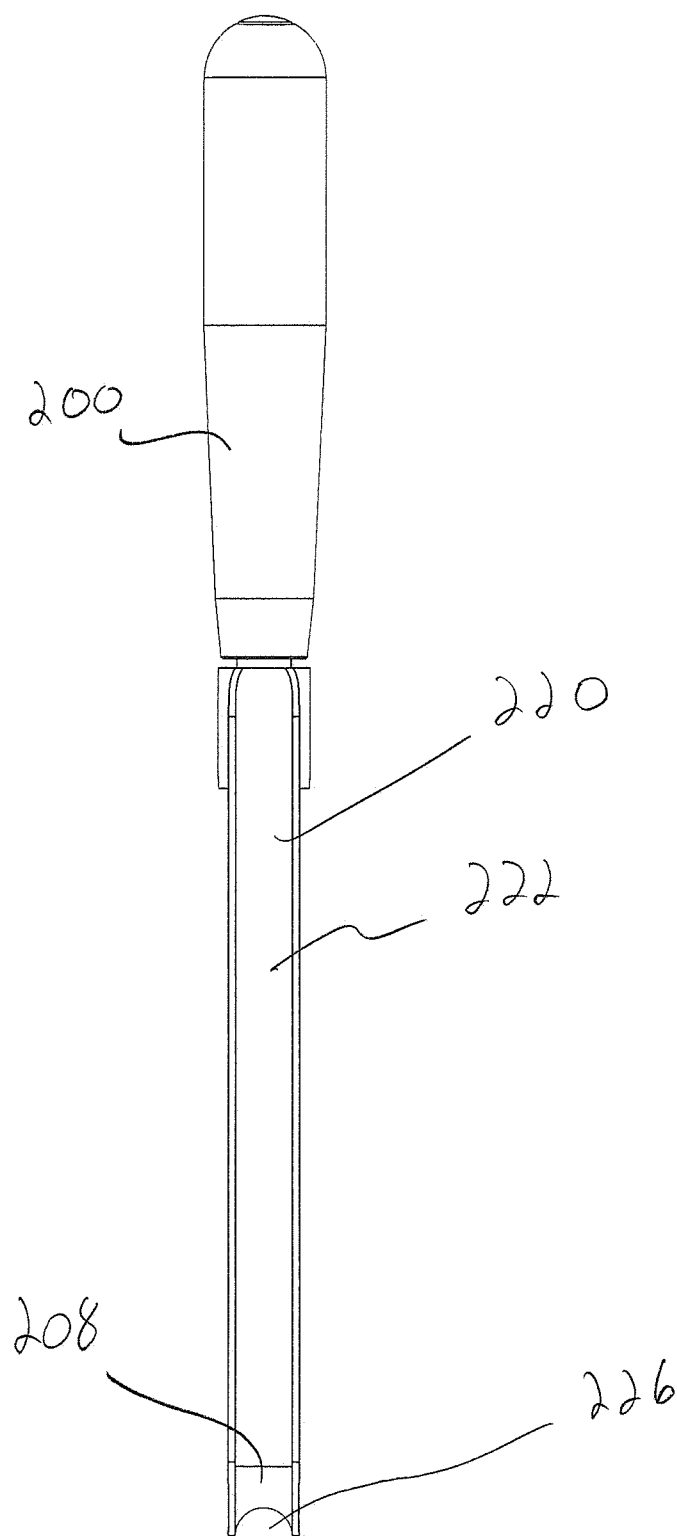
FIG. 16 is a rear elevational view of the bone fusion material guide of FIG. 15 showing a channel of the tip.
Figure 17:
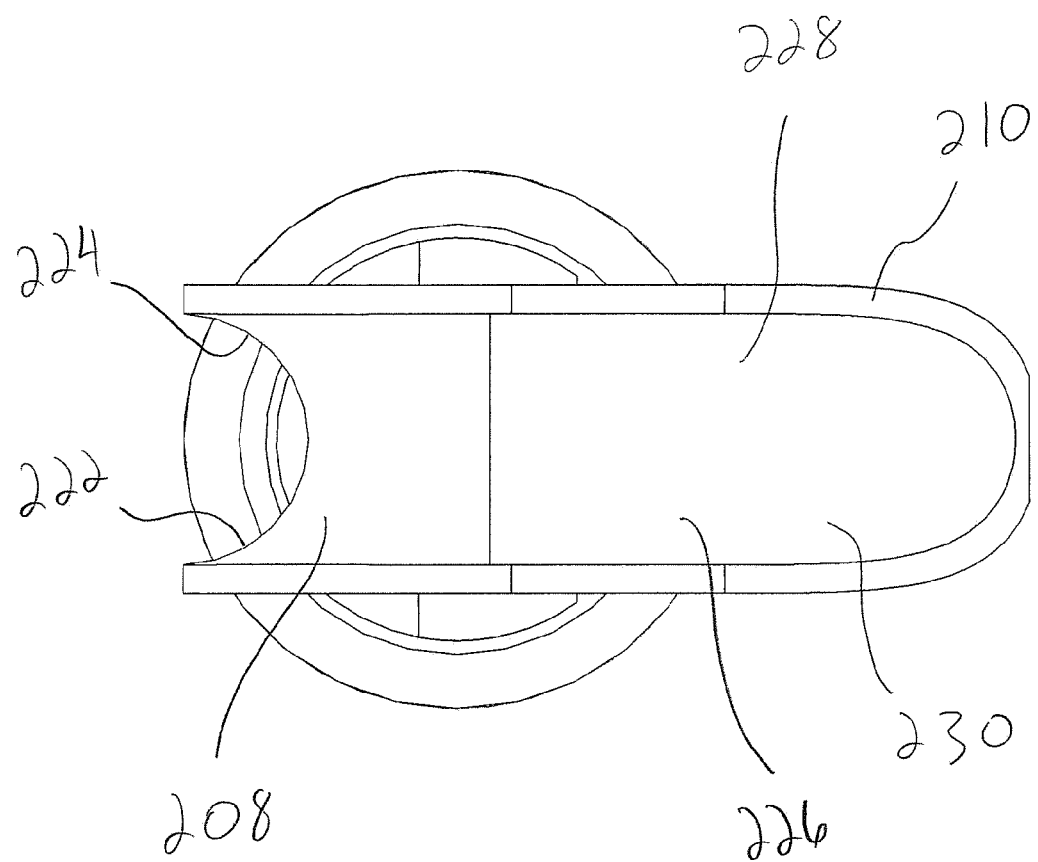
FIG. 17 is a bottom plan view of the bone fusion material guide of FIG. 15 showing a channel of the shaft.

With reference to FIGS. 15-17, a bone fusion material guide 200 is disclosed for directing a delivery instrument, such as the instrument 10 discussed above, toward a bone and directing bone fusion material from the instrument. The bone fusion material guide 200 includes a handle 202 and a depending implement 204. The implement 204 has a shaft 206 extending away from the handle 202, a bend 208, and a tip 210 with an angled chamfered edge 212 configured to separate and sweep tissue out of the path of the tip 210 as the tip 210 is moved into a desired location within the patient.

With reference to FIGS. 16 and 17, the bone fusion material guide 200 has a channel 220 generally extending from the handle 202 toward the angled edge 212. The channel 220 includes a shaft channel portion 222 having a concave surface 224 (see FIG. 17). The concave surface 224 is sized to form a channel through which the distal end 42 of the guide shaft 22 can be advanced toward the tip 210 with minimal interference from surrounding tissues, as discussed below. The guide channel 220 transitions at the bend 208 to a tip channel portion 226 also having a concave surface 228, as shown in FIG. 16. The tip concave surface 228 is sized to form a channel within the patient through which bone fusion material can travel.

With reference to FIG. 15, the shaft 206 has a longitudinal axis 230 and the tip 210 has a tip axis 232 oriented at an angle β relative to the shaft longitudinal axis 230. By orienting the tip 210 to extend at an angle β relative to the longitudinal axis 230, the shaft channel portion 222 permits the distal end 42 of the guide shaft 22 to be advanced in a first direction toward the bone while the tip channel portion 226 redirects the bone fusion material in a second direction transverse to the first direction (see FIGS. 32 and 35). Further, the guide tip 210 functions to lift or distract tissues adjacent the bone to create or maintain a cavity 490 (FIGS. 30-35) in the tissues of the patient through which the bone fusion material can flow, as discussed in greater detail below.

Figure 18:
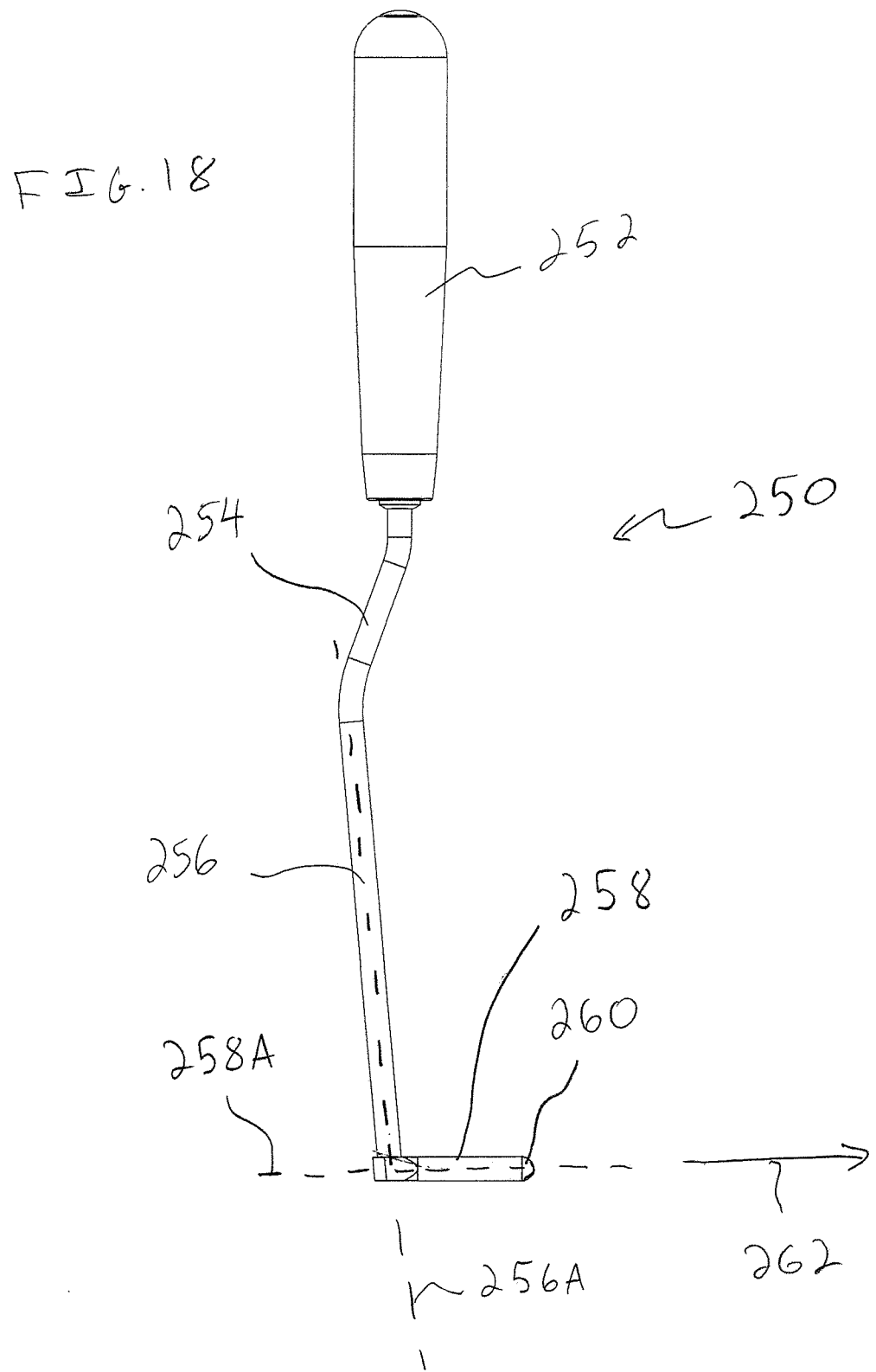
FIG. 18 is a side elevational view of a tissue mover having an elongate shaft and a manipulation member extending generally perpendicular relative to the shaft.

With reference to FIG. 18, a tissue manipulation instrument, such as a tissue mover 250, is provided. The tissue mover 250 has a handle 252 connected to a depending implement 254. The implement 254 includes a shaft 256 having a longitudinal axis 256A and a manipulation member 258 having a longitudinal axis 258A extending generally at a right angle relative to the shaft axis 256A. The manipulation member 258 includes a rounded leading end 260 configured to separate tissues as the leading end 260 is advanced in direction 262 through the patient, as shown in FIG. 18. The implement 254 may be advanced into a small incision in a patient and used to form a subcutaneous, inner cavity 490 near vertebrae 406, 408 (see FIG. 30). The internal cavity 490 is subsequently used to direct bone fusion material within the patient, as discussed in greater detail below.

Figure 19:
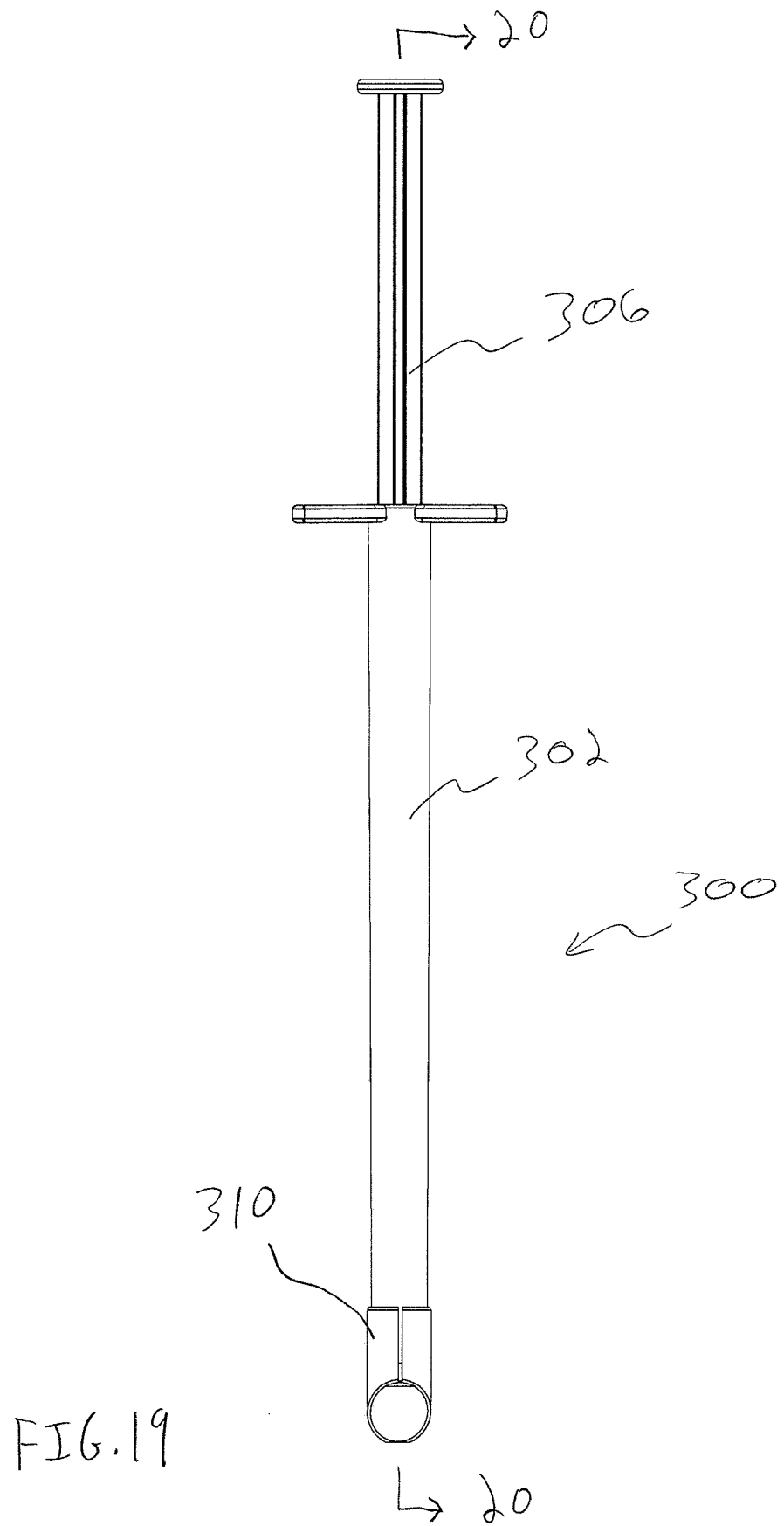
FIG. 19 is an elevational view of a syringe showing a driver and a body of the syringe.
Figure 20:
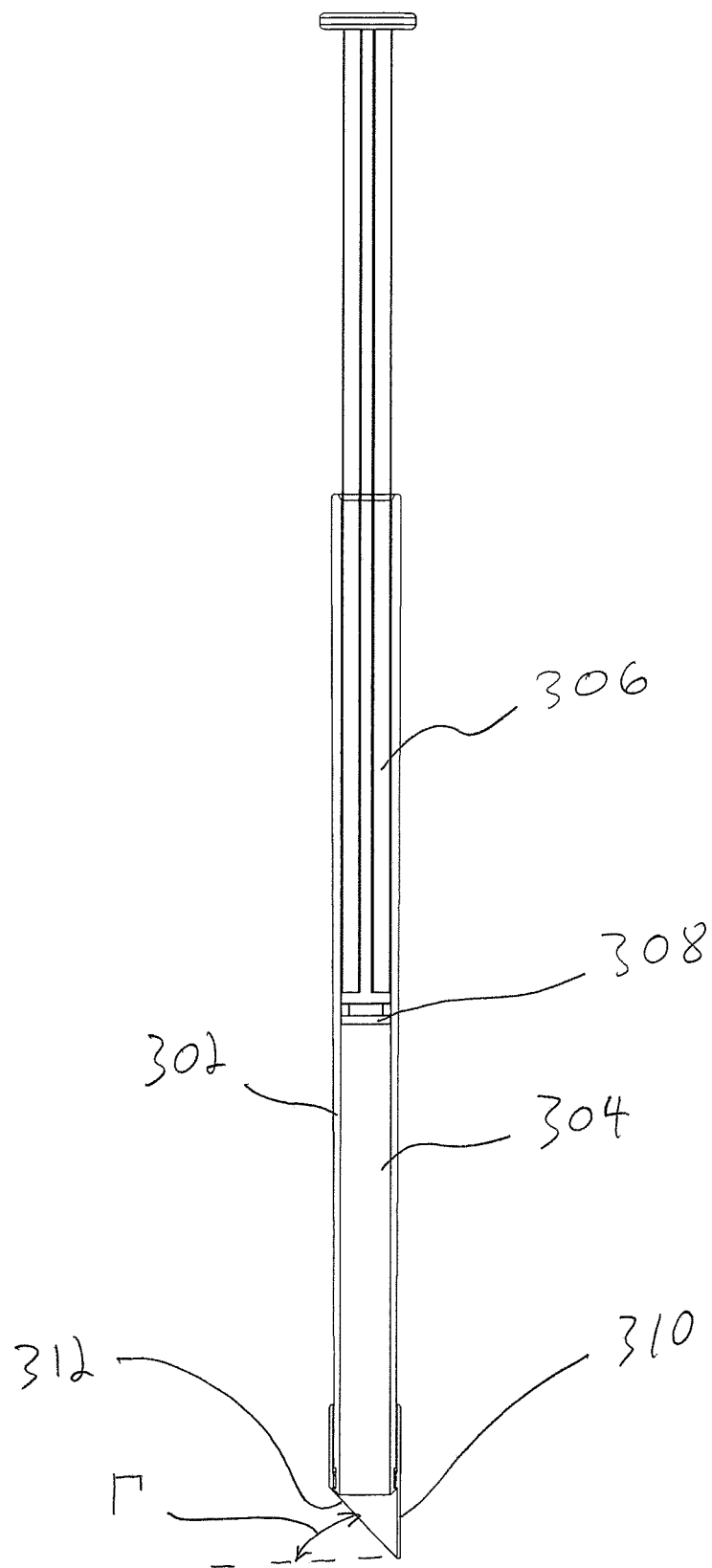
FIG. 20 is a cross-sectional view taken across line 20-20 in FIG. 19 showing an angled tip of the syringe.

With reference to FIGS. 19 and 20, a graft delivery instrument, such as a syringe 300, for delivering bone fusion material is provided. The syringe 300 is similar in a number of ways to the instrument 10 discussed above such that differences between the two will be highlighted. The syringe 300 includes a body 302 having an internal bore 304 filled with a predetermined amount of bone fusion material. The syringe 300 includes a driver 306 with a plunger 308 configured to be advanced through the bore 304 to advance the bone fusion material out from a tip 310 of the syringe 300. With reference to FIG. 20, the tip 310 has a chamfered edge 312 oriented at an angle cc which causes or encourages lateral flow of the bone fusion material from the tip 310, as discussed above with respect to the instrument 10.

Figure 21:
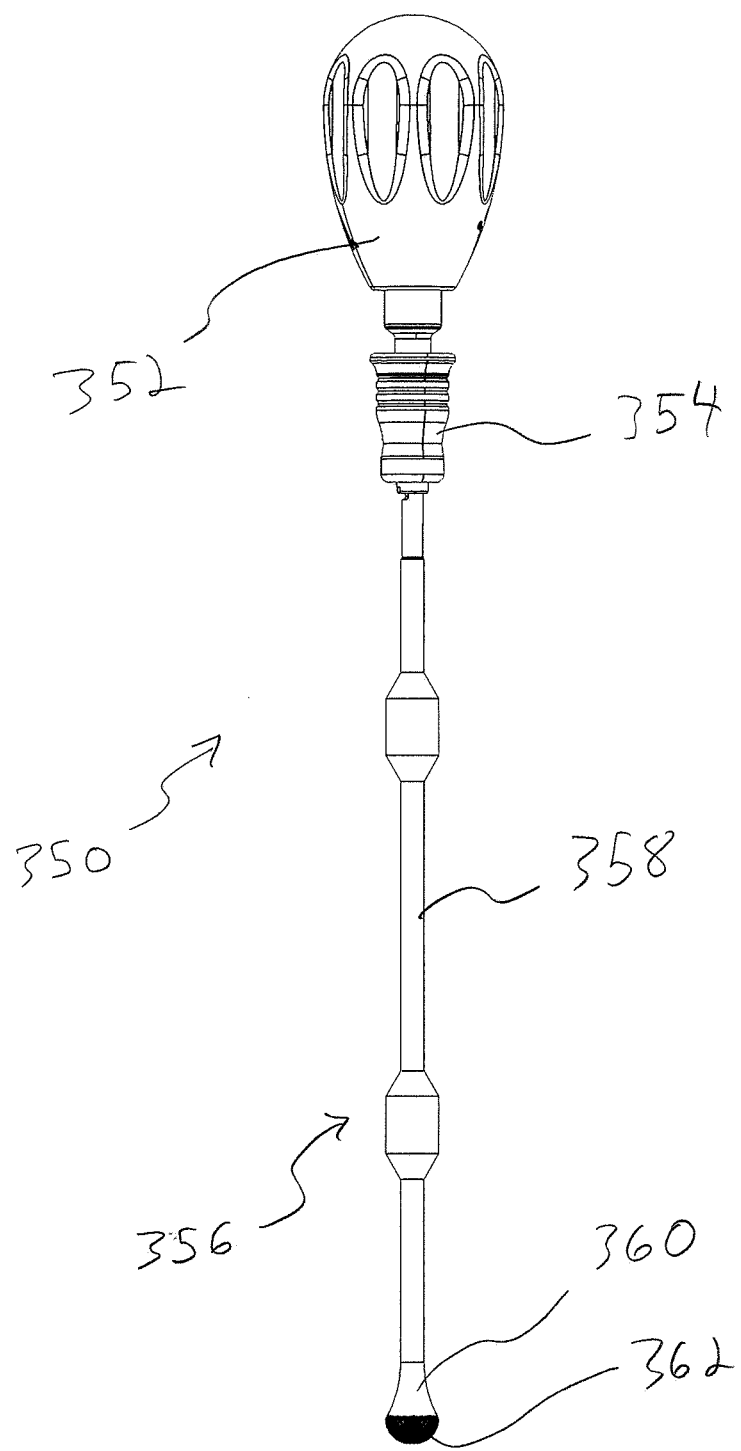
FIG. 21 is an elevational view of bone surface preparation tool including a driver tool having a socket and a burr with an elongate shaft engaged in the socket.

With reference to FIG. 21, a surface preparation tool 350 is shown that includes a driver tool 352 with a socket 354 and a burr 356 received in the socket 354. The burr 356 includes a shaft 358 and a distal head 360 having an abrasive bottom surface portion 362. The burr head 360 is sized to fit into the primary bore 162 of the guide tool 150 (see FIG. 12) and be advanced toward a bone to modify or abrade the surface of the bone, such as to decorticate the bone. The driver tool 352 has a fixed connection between the socket 354 and a handle of the tool 352. In another approach, the driver tool 352 has a ratcheting connection between the handle and the socket 354.

Figure 22:
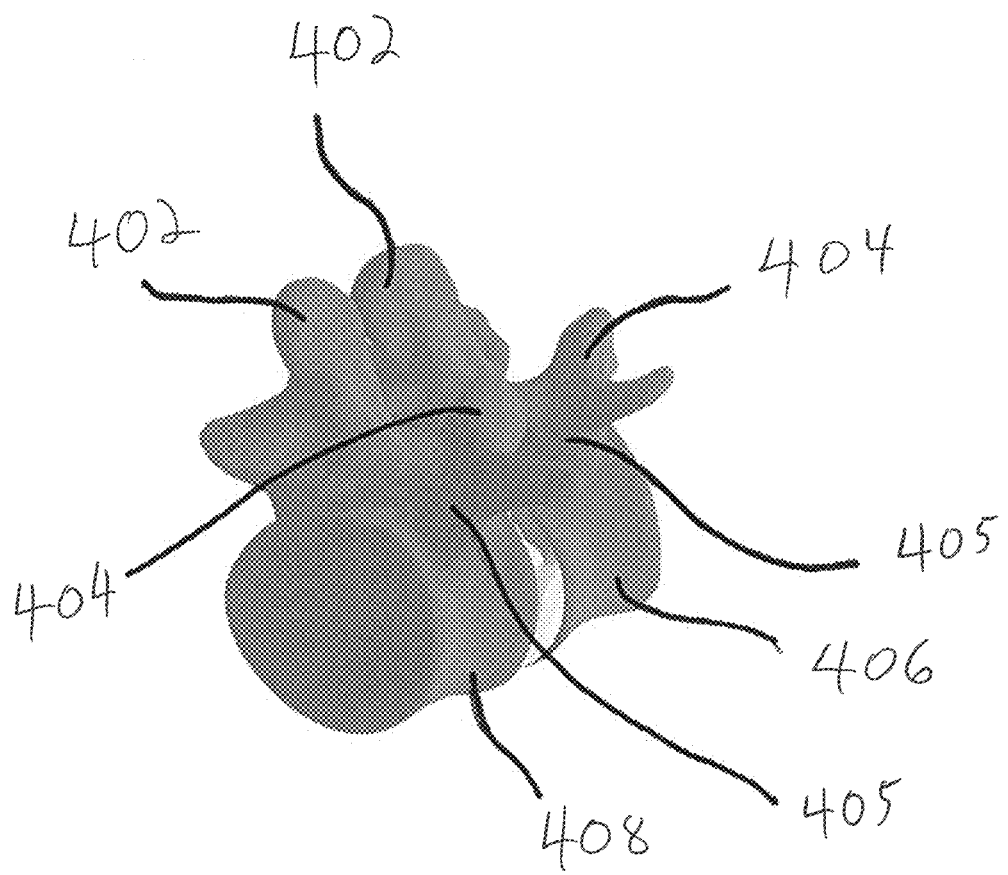

With reference to FIGS. 22-35, a method of fusing vertebrae is shown that includes implanting bone fusion material into the posterolateral gutter between spinous processes 402 and transverse processes 404 of vertebrae 406, 408 (see FIG. 22). Initially, the patient is placed in a prone position and the transverse processes 404 identified using k-wires and fluoroscopy. Small incisions are made in the fascia once the transverse processes 404 of the vertebrae 406, 408 have been identified. Alternatively, the transverse processes 404 may have been located during installation of pedicle screws onto pedicles 405 of the vertebrae 406, 408. In this situation, the incisions for accessing the pedicles 405 may be used to locate the transverse processes 404.

Figure 23:
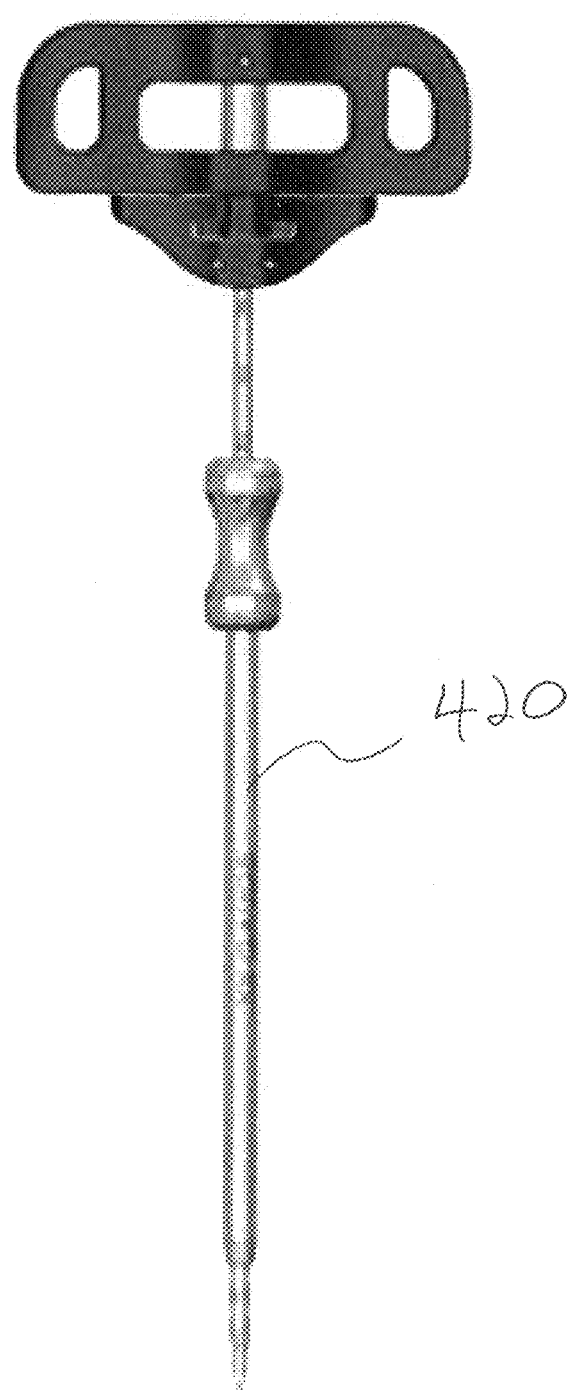
Figure 24:
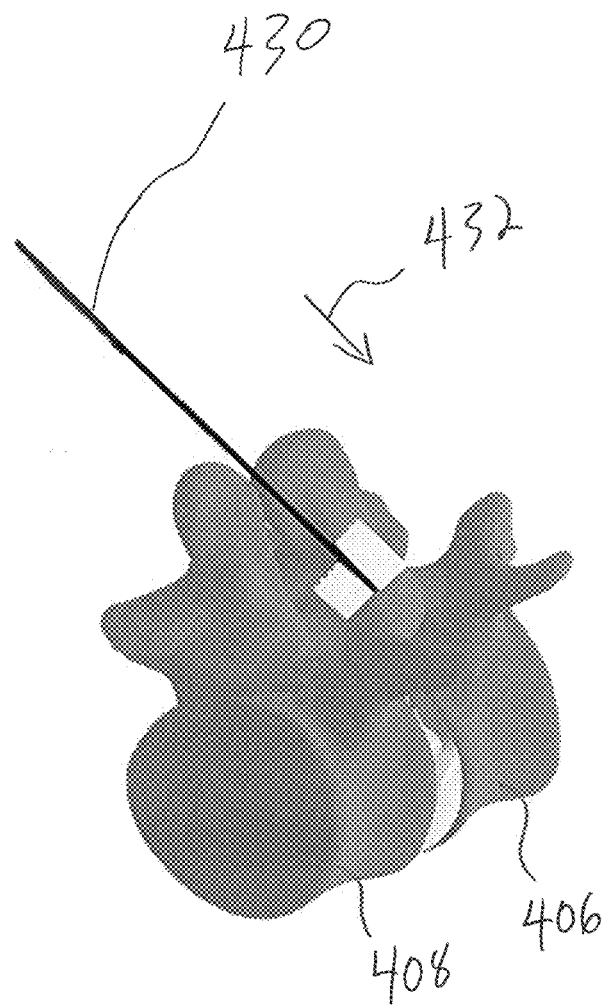

With reference to FIGS. 23 and 24, a targeting needle 420 is driven into the vertebra 406. Next, a guide wire 430 is impacted through the targeting needle 420 and into the vertebra 406, as shown in FIG. 24. Next, the tissue surrounding the location of the guide wire 430 in the vertebrae 406 is dissected as desired.

Figure 25:
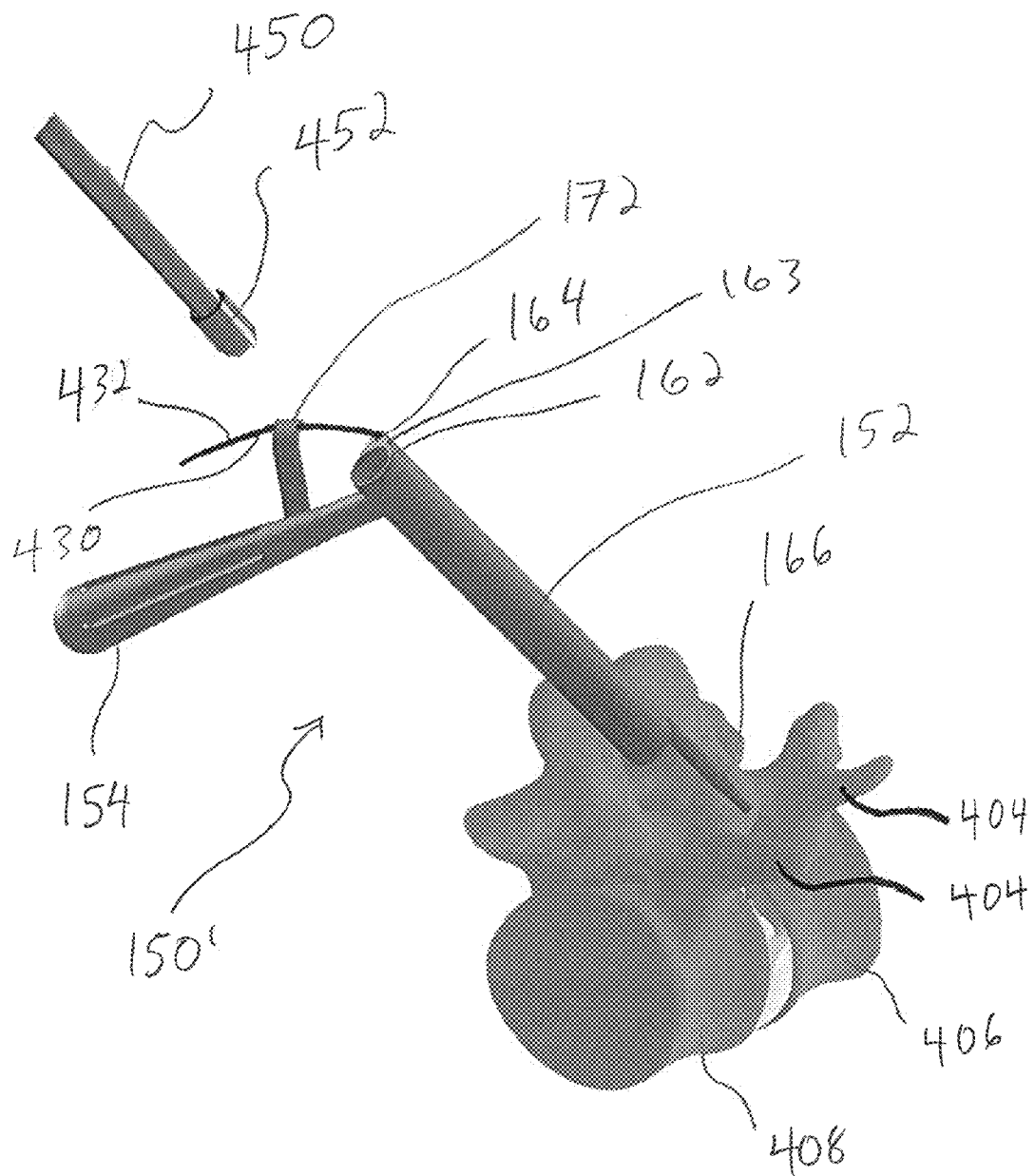
Figure 26:
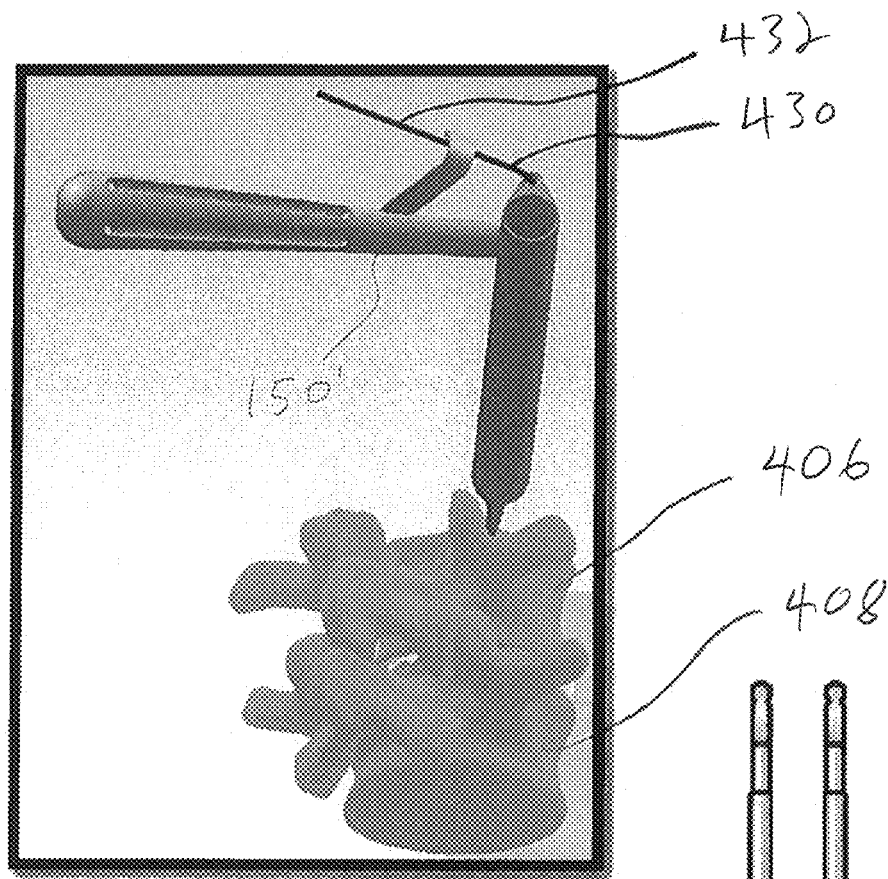

With reference to FIG. 25, a proximal end 432 of the guide wire 430 is inserted into the secondary bore 164 of the guide tool 150' and the guide tool 150' is slid down the guide wire 430 toward the vertebra 406. (The guide tool 150' shown in FIGS. 22-29 is substantially similar to guide tool 150 such that similar reference numerals will be used to represent similar parts of the tools 150, 150'.) The guide tool 150' is advanced along the guide wire 430 until the tip 166 reaches the pedicle 405 of the vertebra 406. A mallet may be used to tap a flat upper surface 163 of the guide tool 150' and drive the tip 166 into engagement with the pedicle 405. Fluoroscopy may be used to verify the position of the tip 166. The proximal end 432 of the guide wire 430 may then be slightly bent to position the proximal end 432 in the hook opening 172 of the guide tool 150, as shown in FIGS. 25 and 26.

Figure 27:
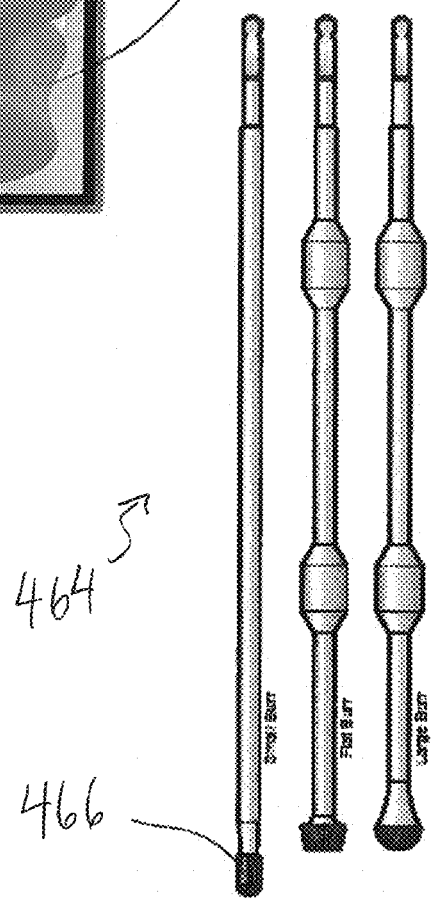
Figure 29:
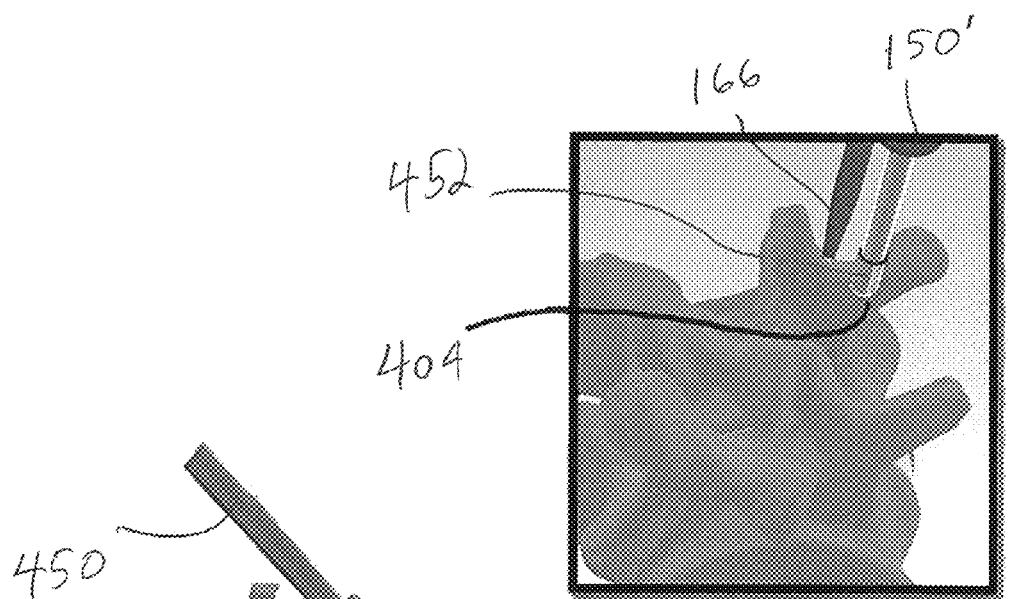
Figure 28:
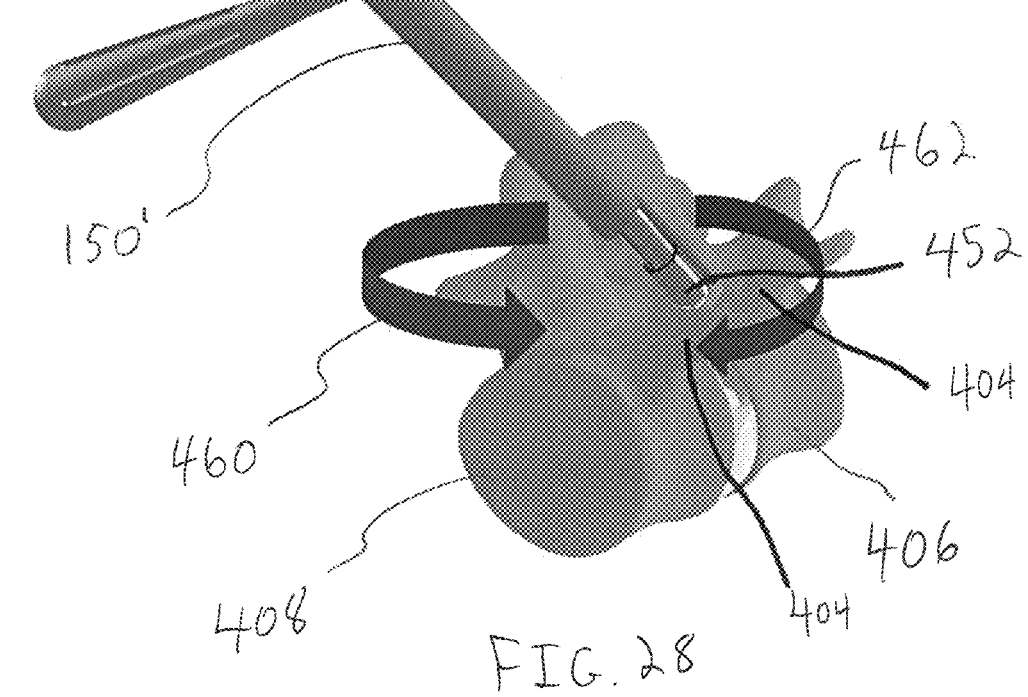

With continuing reference to FIG. 25, a burr 450 similar to burr 356 is advanced into the primary bore 162 of the guide tool 150'. The burr 450 is advanced along the primary bore 162 until a distal preparation end surface 452 reaches the transverse process 404 of the vertebra 406, as shown in FIGS. 28 and 29. With the burr end surface 452 in contact with the transverse process 404, the burr 450 may be rotated in directions 460, 462 about the longitudinal axis of the burr 450 to engage the transverse process 404 and remove cortical bone therefrom. Depending on the application, the burr 450 may be replaced with or supplemented by differently shaped burrs 464, as shown in FIG. 27. The burrs 464 have different heads 466 for performing different surface preparation techniques. It will be apparent that instruments other than burrs can be advanced through the primary bore 162 to the surgical site. For example, an instrument having a distal end portion without cutting teeth may be used to displace soft tissues proximate the transverse process 404 prior to using the burr 450 to cut the transverse process 404.

Once the surface of the transverse process 404 has been sufficiently prepared, the burr 450 is withdrawn from the primary bore 162 of the guide tool 150'. This process is repeated to prepare the surface of the transverse process 404 of the other vertebra 408, including inserting a guide wire 431 into the vertebra 408, advancing the guide tool 150' along the guide wire 431, and using the burr 450 to prepare the surface of the transverse process 404 of the other vertebra 408.

With reference to FIGS. 30 and 31, the manipulation member 258 of the tissue mover 250 is advanced in direction 413 through a percutaneous incision 415 and generally along the guide wire 431 toward the transverse process 404 of the vertebrae 408, as shown in FIG. 30. It will be apparent that a tubular member and/or another device, such as a retractor, may be used to enlarge the incision 415 and permit the manipulation member 258 to travel therethrough. The handle 252 of the tissue mover 250 is manipulated to redirect and advance the rounded leading end 260 in direction 480 toward the transverse process 404 of the vertebra 406. Advancing the rounded leading end 260 toward the transverse process 404 of the vertebra 406 sweeps tissues away from the posterolateral gutter and the transverse processes 404. Further, advancing the leading end 260 separates tissues and creates an internal cavity 490 that extends along the posterolateral gutter between the transverse processes 404. As discussed in greater detail below, the bone fusion material is injected into the cavity 490 and the cavity 490 functions as a path of least resistance to direct the bone fusion material from one transverse process 404 to another. Once the tissue mover 250 and leading end 260 thereof have formed the cavity 490, the tissue mover 250 is removed from the incision 415 before the bone fusion guide 200 is advanced into the incision. Alternatively, the tissue mover 250 may remain in the patient to maintain the internal cavity 490 as the tip 210 of the bone fusion guide 200 is advanced through the incision 415 and into the cavity 490.

In one approach, the tissue mover 250 may only need to be used in one direction to form a cavity (as shown in FIG. 30). In another approach, the tissue mover 250 is withdrawn from the incision 415, advanced into an incision 417 associated with the vertebra 406, and rounded leading end 260 is advanced toward the transverse process 404 of the vertebra 406. Next, the handle 252 is manipulated to redirect the rounded leading end 260 in direction 484 from the transverse process 404 of the vertebra 406 toward the transverse process 404 of the vertebra 408 to form the cavity 490 from the opposite side. The tissue member 252 may also be moved vertically in directions 482 in order to lift and move tissues. Further, the handle 252 may be manipulated to steer the rounded end 260 around boney structures with the user receiving tactile feedback while he or she steers the rounded end 260.

With reference to FIG. 31, the bone fusion material guide 200 is advanced into position near the transverse process 404 of the vertebra 406 in a manner similar to the tissue mover 250. For example, the tip 210 is advanced through an incision 417, toward the transverse process 404 of the vertebra 406, and redirected in direction 484 toward the transverse process 404 of the vertebra 408. The guide channel portion 220 receives the guide wire 430 and provides some clearance for the user to manipulate the bone fusion material guide 200 as the tip 210 is advanced into position. The tip 210 of the bone fusion material guide 200 is positioned in the posterolateral gutter and within the cavity 490 formed by the tissue mover 250, as shown in FIG. 31.

Figure 32A:
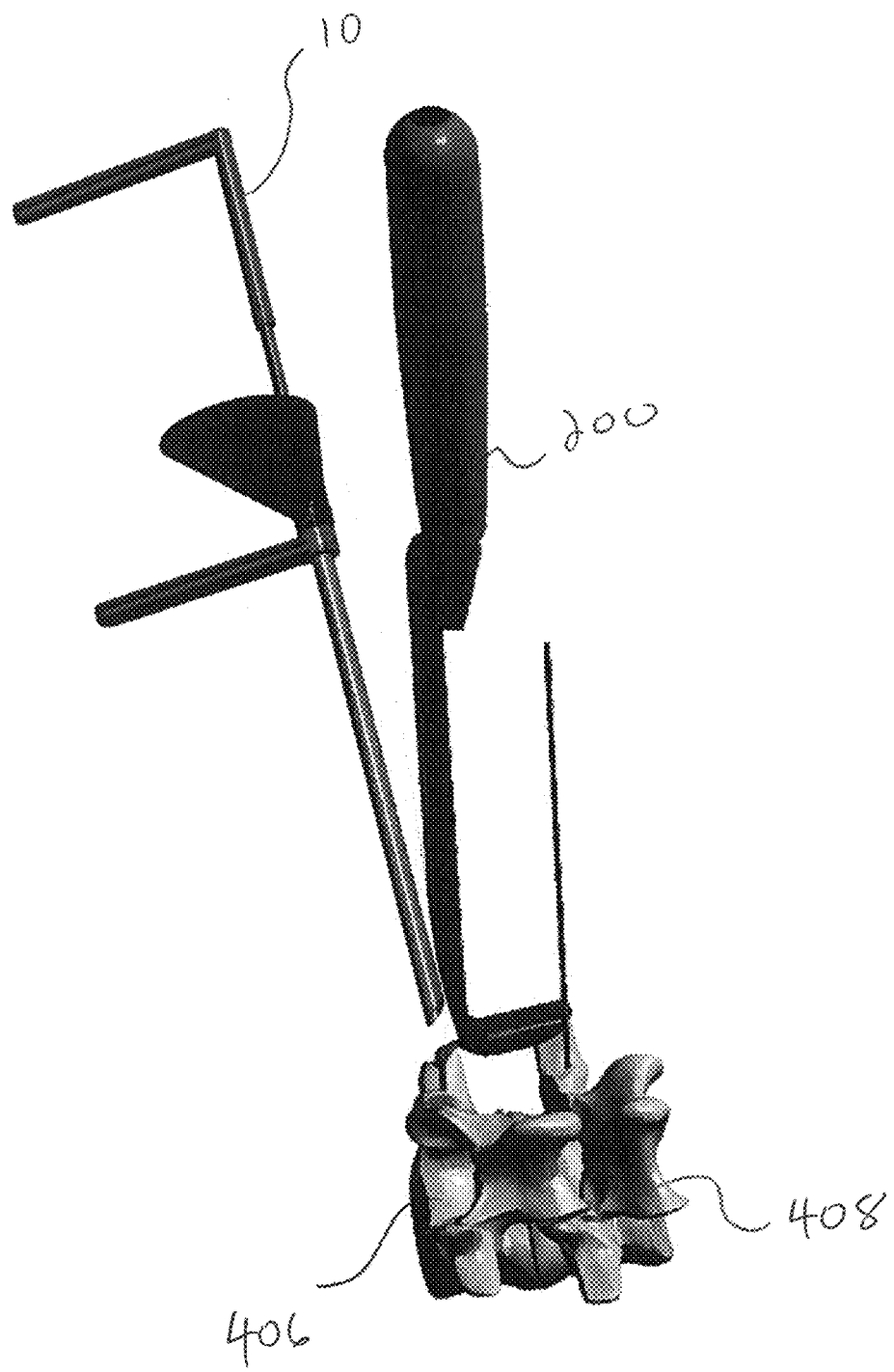

With reference to FIG. 32, the tip 310 of the syringe 300 is advanced in direction 501 into the incision 417 and along the shaft channel portion 222 until reaching the transverse process 404 of the vertebra 406. The syringe 300 is preloaded with bone fusion material 500 such as autograft or bone fusion material. With reference to FIGS. 33 and 34, the bone fusion material guide tip 210 extends along an upper boundary of the cavity 490 and restricts the tissues from collapsing. Further, the syringe tip 310 with its angled opening 312 is positioned to direct the bone fusion material 500 in direction 502 into and along the cavity 490. FIG. 32A shows the instrument 10 being used in place of the syringe 300.

With reference to FIG. 35, the driver 306 is shifted toward along the syringe body bore 304 to discharge approximately half of the bone fusion material 500 in direction 502 through the cavity 490 from the transverse process 404 of the vertebra 406 toward the transverse processes 404 of the vertebra 408. As discussed above with respect to instrument 10, the angled tip 310 of the syringe 300 directs the bone fusion material 500 in a direction 502 transverse to a longitudinal axis of the syringe 300.

Figure 36:
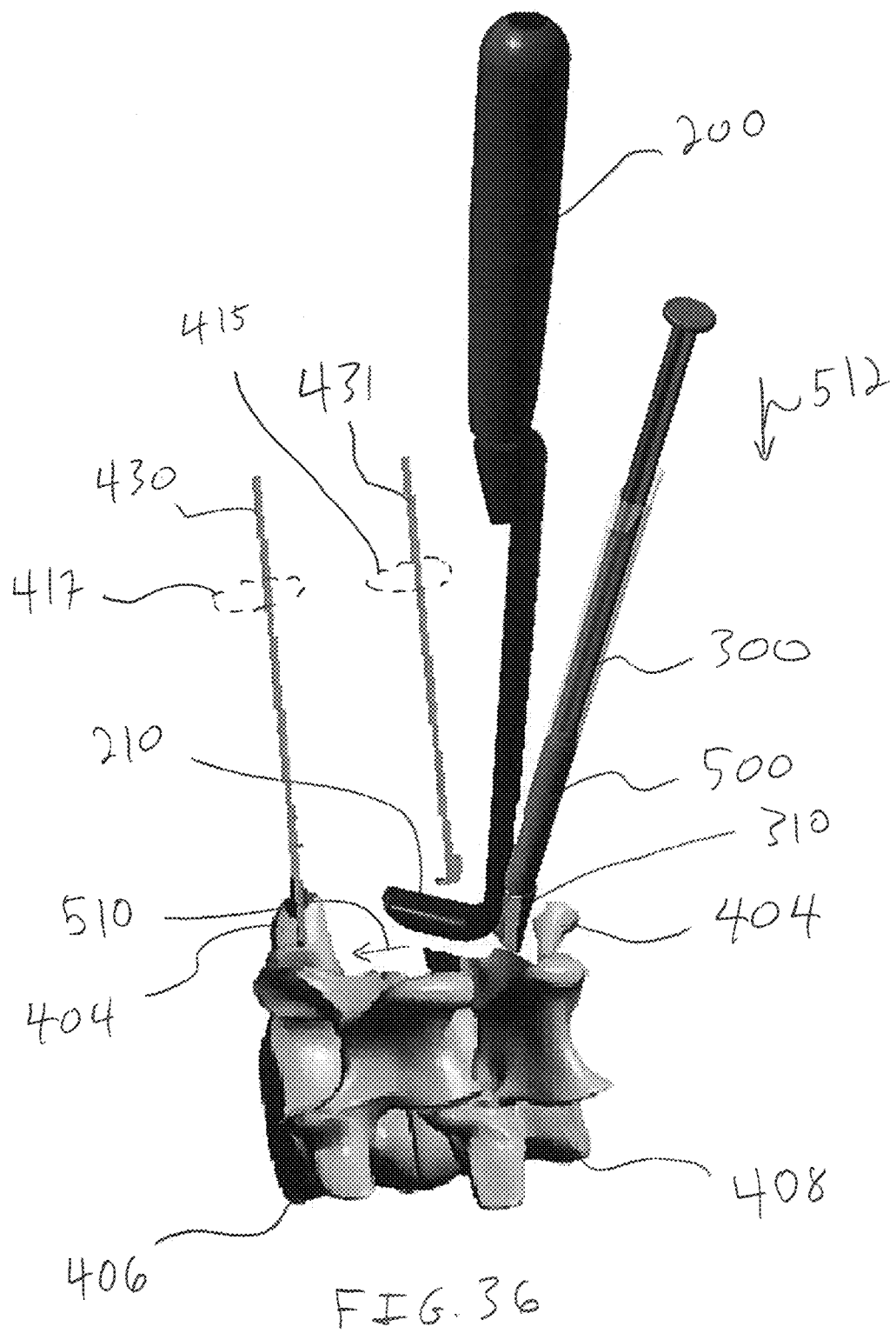

With reference to FIG. 36, the bone fusion material guide 200 is removed from the incision 417 near the guide wire 430 and is turned 180 degrees about its longitudinal axis so that its bone fusion material guide tip 210 faces in an opposite direction i.e., from vertebrae 408 toward vertebrae 406. The guide tip 210 is then advanced through incision 415 and along guide wire 431 into position near the transverse process 404 of the vertebrae 408 before being redirected in direction 510 toward the vertebrae 406, as shown in FIG. 36. The syringe tip 310 is then advanced downward along the shaft channel portion 222 in direction 512 toward the vertebra 408. The remainder of the bone fusion material 500 is then discharged from the syringe 300 in direction 510 from the transverse process 404 of the vertebra 408 toward the transverse process 404 of the vertebra 406. The two bodies of the bone fusion material 500 meet generally in the middle of the cavity 490 between the transverse processes 404 of the vertebrae 406, 408. The instruments and guide wires may then be removed from the patient and the bone fusion material 500 permitted to bond with the transverse process 404. In another approach, the user can fill the cavity 490 by injecting the bone fusion material 500 from only one side of the cavity 490, such as from the position of the syringe 300 shown in FIG. 32.

Figure 37:
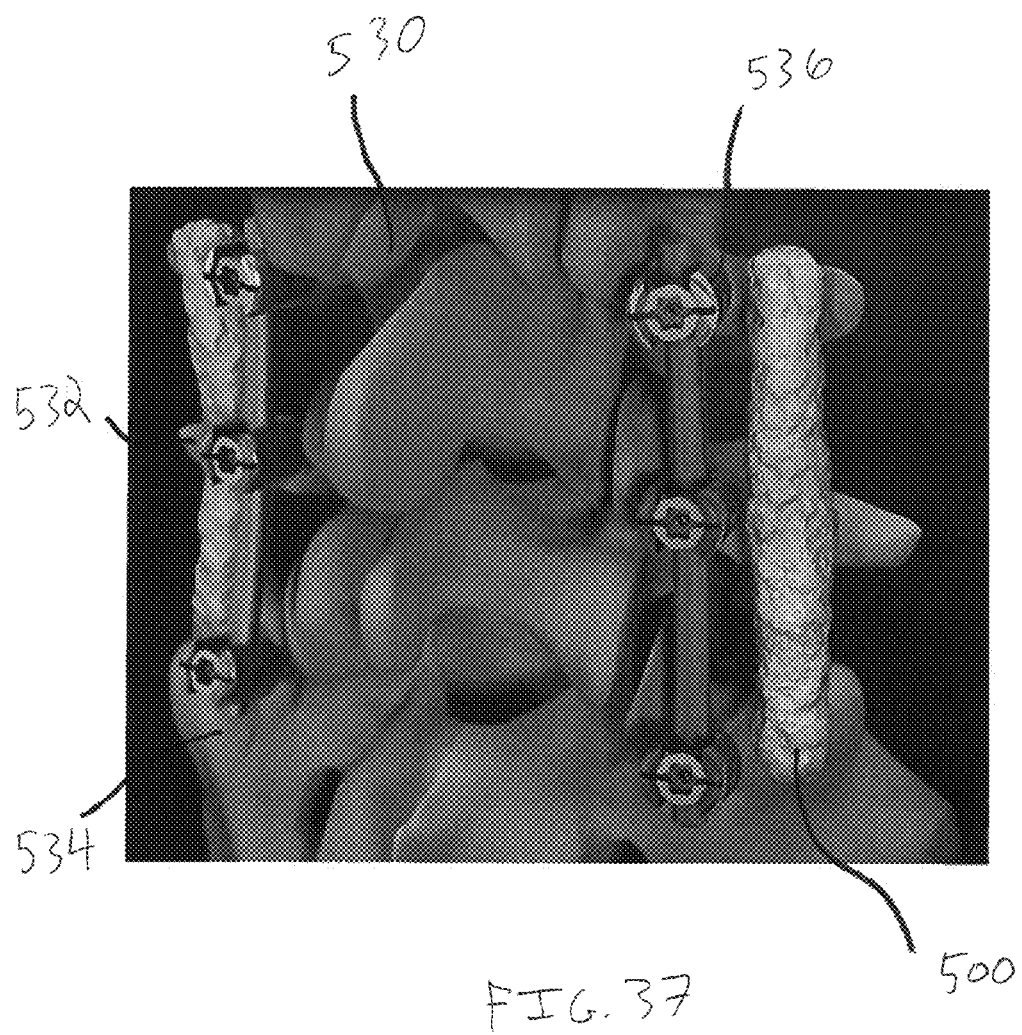
FIG. 37 is a perspective view of a posterolateral fusion utilizing pedicle screw systems and bone fusion material to stabilize the vertebrae.

With reference to FIG. 37, the foregoing method was used to implant bone fusion material 500 on vertebrae 530, 532, 534. The bone fusion material 500 encourages bone fusion between the vertebrae 530, 532, 534 and supplements the stabilization provided by the pedicle screw systems 536.

Figure 38:
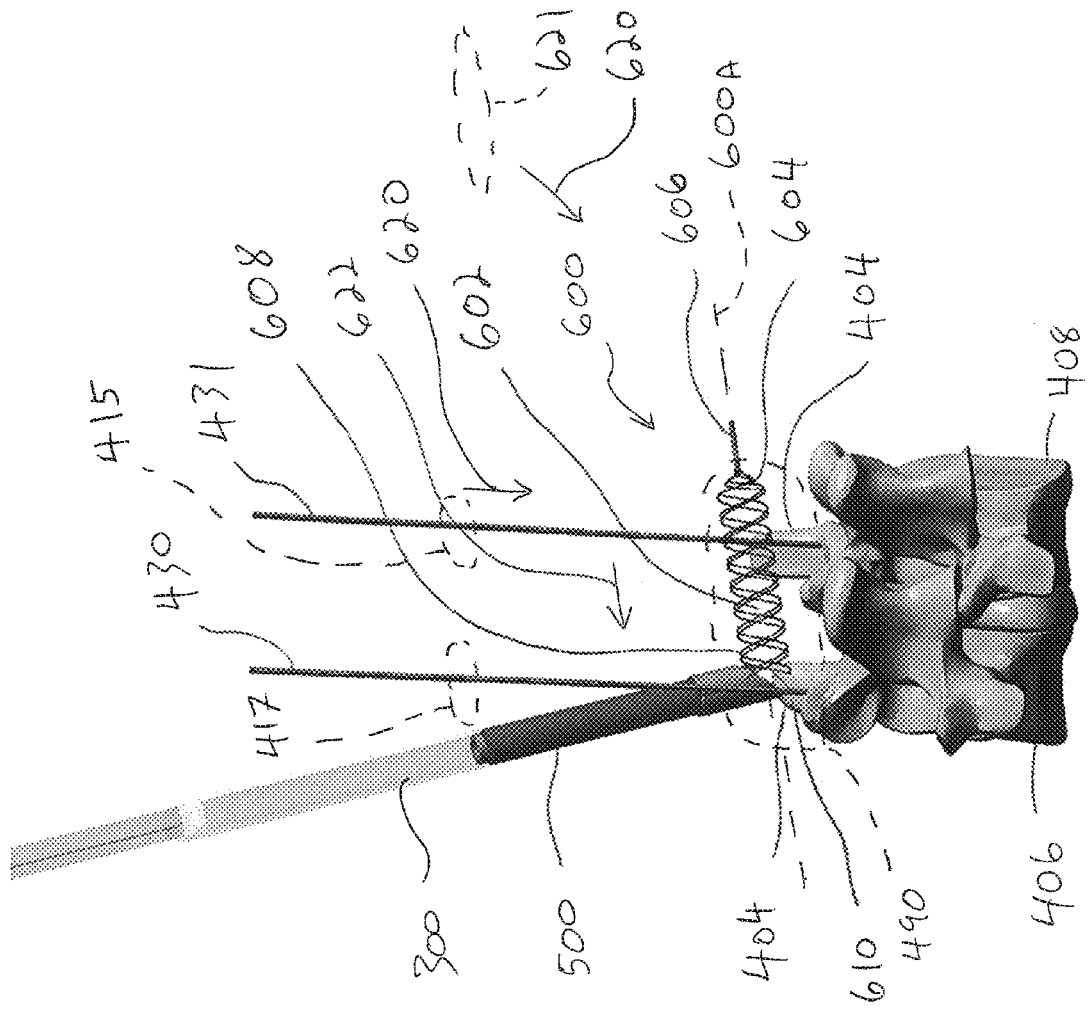
FIG. 38 is a perspective view of an expanded stent in the posterolateral gutter between the spinous processes and the transverse processes of vertebrae and a syringe positioned to direct bone fusion material into a compartment of the stent.
Figure 39:
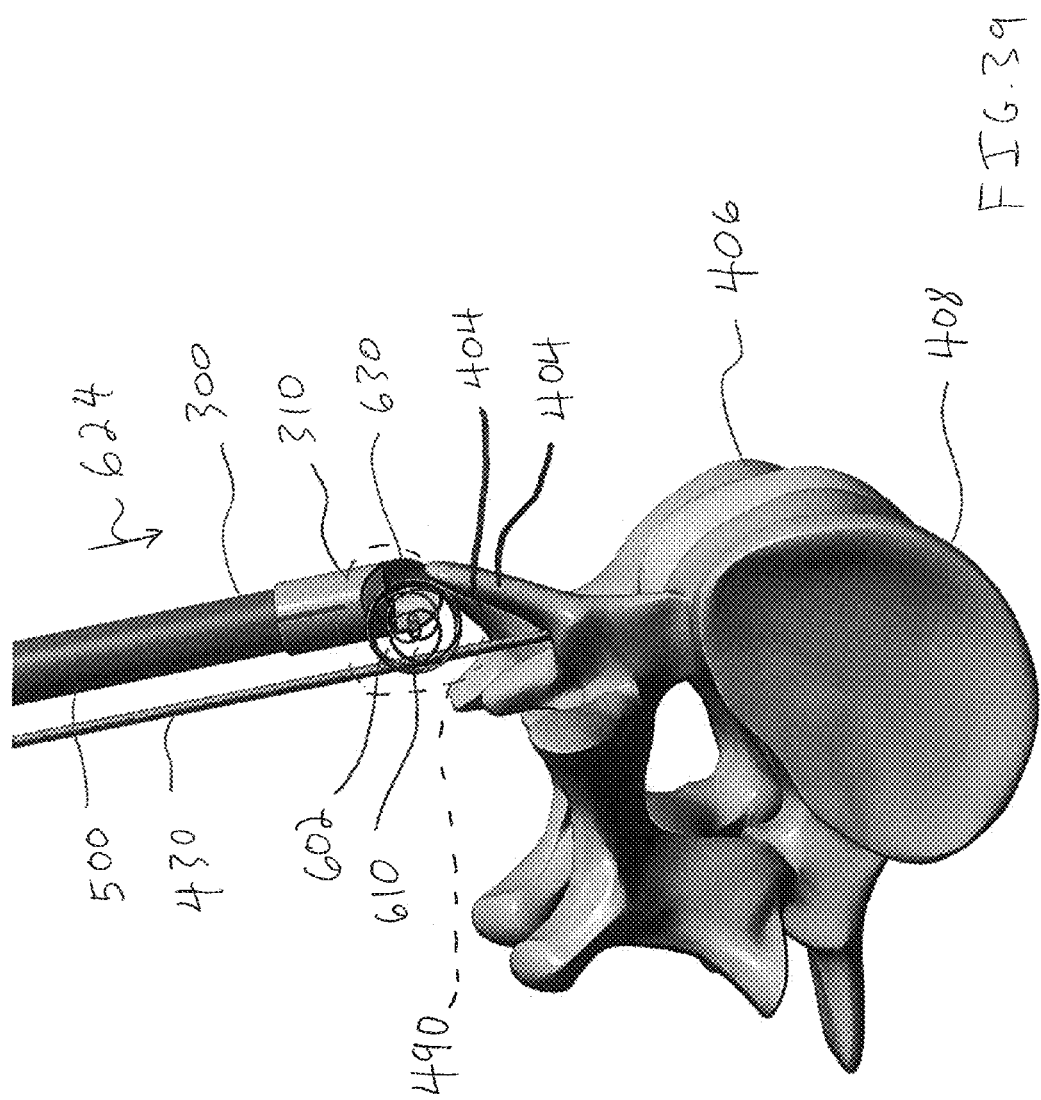
FIG. 39 is a perspective view of the stent and syringe of FIG. 38 showing a tip of the syringe positioned to direct bone fusion material into an opening of the stent compartment.

With reference to FIGS. 38 and 39, an expansion device, such as a stent 600, is shown that expands soft tissues. The stent 600 may be used with or in place of the tissue mover 250 and the bone fusion material guide 200 discussed above to establish and maintain the subcutaneous cavity 490. The stent 600 has an insertion configuration where the cross-section of the stent 600 transverse to an axis 600a thereof is reduced to permit the stent to be advanced into the patient. The stent 600 may be shifted to an expanded configuration that provides a relatively large internal compartment 602 along which the graft 500 can travel. Shifting the stent 600 to the expanded configuration may retract tissues and form at least a portion of the cavity 490. In another approach, the cavity 490 is formed by separating tissues using the tissue mover 250 and/or bone fusion material guide 200 as discussed above. In this approach, shifting the stent 600 to its expanded configuration maintains the size of the cavity 490 and resists the tissues from pulling back together and collapsing the cavity 490.

The stent internal compartment 602 receives the bone fusion material 500 from the instrument 10 and/or the syringe 300. In some applications, the stent 600 may be left in the patient and includes openings through which bone can grow into the bone fusion material 500 present in the stent compartment 602. In another approach discussed in greater detail below, the stent 600 is withdrawn from the surgical site once the bone fusion material 500 has been injected into the stent compartment 602. This leaves a generally column-shaped mass of the bone fusion material 500 within the patient (without the stent 600) to fuse with the transverse processes 404 of the vertebrae 406, 408.

The stent 600 has a proximal end 604 with a steering rod 606 that can be manipulated to adjust the orientation or position of the stent 600 during insertion and positioning of the stent 600 near the vertebrae 406, 408. The stent 600 has a distal end 608 with an opening 610 that opens to the compartment 602. By positioning the stent opening 610 opposite the stent steering rod 606, the stent compartment 602 may be easily filled using the syringe 300 advanced along the guide rod 430, as shown in FIG. 38.

To position the stent 600, the stent distal end 608 is initially advanced in direction 620 through an incision 621, toward the vertebra 408, and then advanced in direction 622 toward the vertebra 406. Once the stent 600 is in position, the stent 600 is shifted to its expanded configuration which enlarges the opening 610 and the compartment 602. In one approach, shifting the stent 600 to its expanded configuration also retracts tissues around the stent 600 and enlarges the cavity 490.

With reference to FIG. 39, the syringe 300 is advanced in direction 624 downward along the guide wire 430 until the tip 310 is positioned near the vertebra 406, as discussed above with respect to FIGS. 32-34 (the bone fusion material guide 200 may or may not be used). As shown in FIG. 39, the tip 310 has an opening 630 that is aligned with the opening 610 of the stent compartment 602 so that the bone fusion material 500 can be discharged from the syringe 300 and into the compartment 602.

The stent 600 may be a self-expanding stent, such as a stent made from a resilient material that is initially compressed and then expands upon removal of the compressive force therefrom. In another approach, the stent 600 is made of nitinol having shape memory properties that cause the stent 600 to expand and/or phase change upon implantation into the patient's body due to the elevated internal temperature of the patient. The stent 600 may also be made of a polymer, a metal such as stainless steel or titanium, and alloys such as nickel-titanium blends. In another approach, the stent 600 is made of a re-absorbable polymer, such as PLA and PLGA including braided/woven biodegradable fibers. To visualize the position of the stent 600 within the patient, the stent 600 may contain radiopaque marker bands or have radiopaque stent material.

Figure 40:
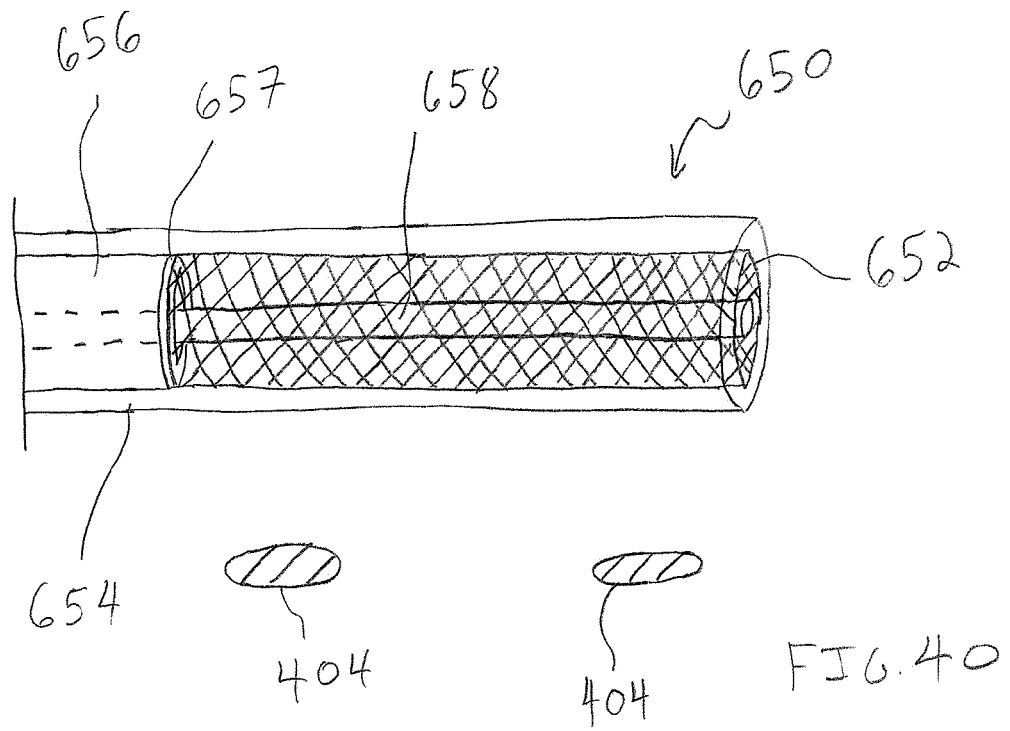
FIG. 40 is a schematic view of a stent delivery instrument positioned near transverse processes of a pair of vertebrae.
Figure 41:
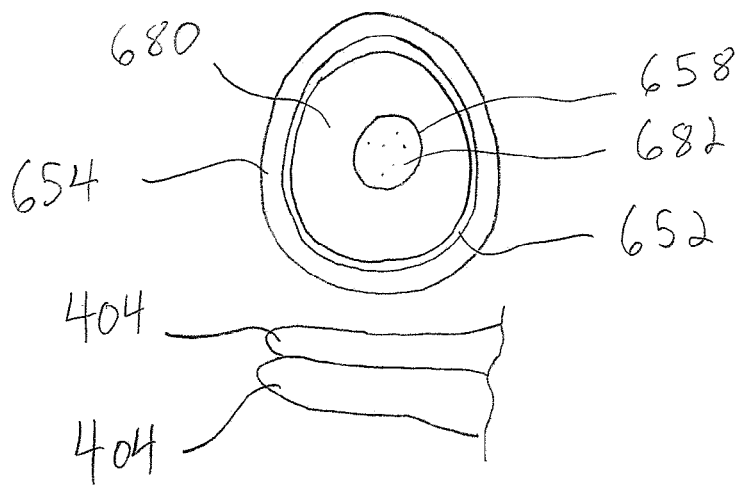
FIG. 41 is a front view of the stent delivery instrument of FIG. 40 and the transverse processes.

With reference to FIGS. 40 and 41, an expansion device delivery instrument 650 is shown for maneuvering an expansion device, such as a stent 652, into position near the vertebrae 406, 408. The delivery instrument 650 includes a guide, such as a catheter 654, a support, such as a support tube 656, and a delivery device, such as a bone fusion material delivery tube 658. (The catheter 654 is illustrated as being made of a transparent material to show the operation of the support tube 656 and delivery tube 658.)

With reference to FIGS. 40 and 41, the stent 652 is a self-expanding stent and the catheter 654 encircles the stent 652 thereby restricting outward expansion of the stent 652 during movement of the delivery instrument 650 into position near the vertebrae 406, 408. In this insertion configuration, the stent 600 may have a compartment 680 with the graft delivery tube 658 extending therein, as shown in FIG. 41. In another form, the stent compartment 680 tightly encircles the bone fusion material delivery tube 658 when the stent 600 is in the insertion configuration so that an inner surface of the stent 600 is in contact with an outer surface of the bone fusion material delivery tube 658. The bone fusion material delivery tube 658 may contain bone fusion material 682 or, as another example, the bone fusion material 682 may be advanced into delivery tube 658 upon the delivery instrument 650 reaching the desired position near the vertebrae 406, 408.

Figure 42:
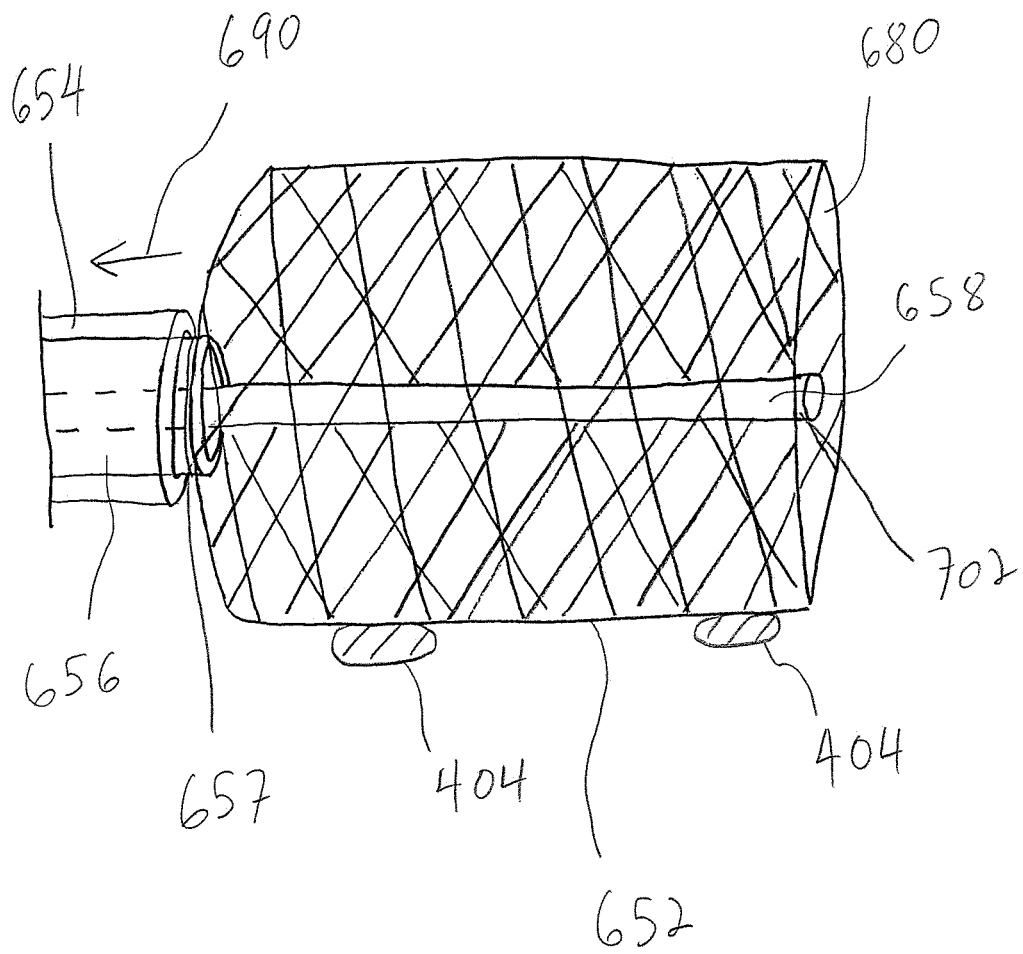
FIG. 42 is a schematic view of the stent device delivery instrument of FIG. 40 showing a catheter of the instrument retracted away from the stent which permits the stent to expand and a bone fusion material delivery tube extending along the compartment of the stent.

With reference to FIG. 42, the catheter 654 is retracted in direction 690 away from and off of the stent 652. This permits the stent 652 to shift to its expanded configuration. Although the stent 652 is expanded, the stent 652 remains coupled to the support tube 656 via a connection 657. The connection 657 may take the form of, for example, a friction fit between the stent 652 and the support tube 656. In another approach, the connection 657 can include an adhesive, weld, or one or more fasteners.

Figure 43:
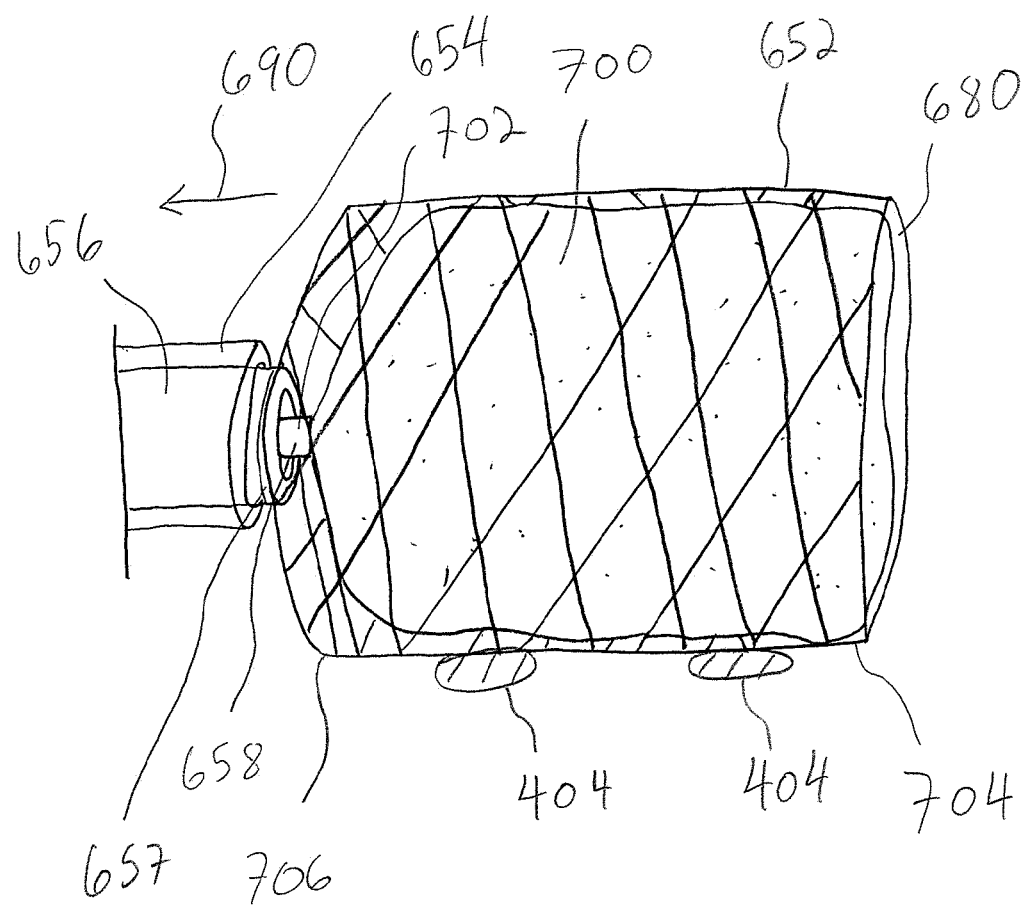
FIG. 43 is a schematic view similar to FIG. 42 showing the stent compartment filled with bone fusion material and the bone fusion material delivery tube retracted.

With reference to FIG. 43, the graft delivery tube 658 is retracted in direction 690 into the catheter 654 as bone fusion material 682 is discharged from an end 702 of the delivery tube 658. Discharging the bone fusion material 682 concurrently with retracting the delivery tube 658 positions the bone fusion material 682 at a distal end 704 of the stent 652 and continues filling the compartment 680 until the tube 658 reaches a proximal end 706 of the stent 652. In this manner, the compartment 680 may be fully filled with the bone fusion material 682.

Figure 44:
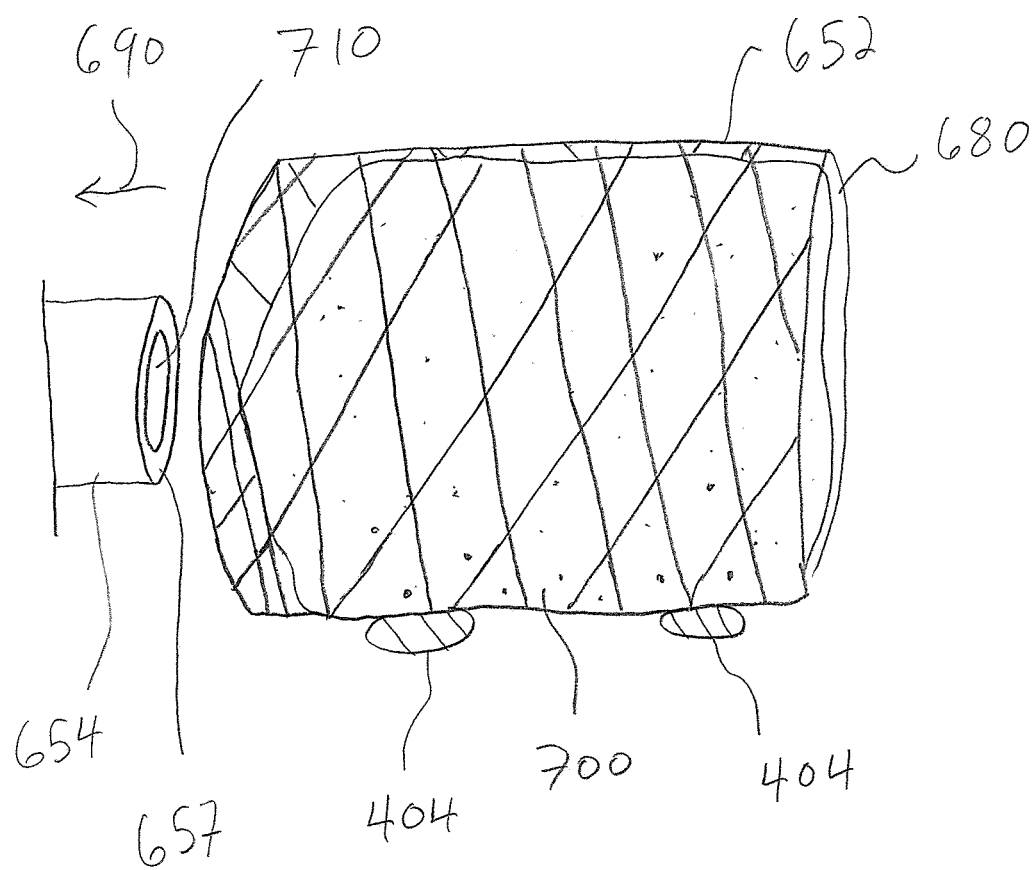
FIG. 44 is a schematic view similar to FIG. 42 showing a catheter of the instrument spaced from the stent after a support tube of the instrument has been disconnected from the stent and retracted away from the stent through the catheter.

Next, the connection 657 between the support tube 656 and the stent 652 is disconnected, as shown in FIG. 44. Disconnecting the stent 652 from the support tube 656 may include disengaging a friction fit connection 657 between the stent 652 and support tube 656, for example. In another form, the connection 657 may be a frangible member extending between the stent 652 and the support tube 656. Disconnecting the stent 652 from the support tube 656 in this approach may involve applying sufficient tension or torsion to the frangible member to fracture the frangible member and disconnect the stent 652 from the support tube 656. The support tube 656 is then withdrawn in direction 690 away from the stent 652 and upward through a cannula 710 of the catheter 654 outward from the patient, as shown in FIG. 44. The catheter 654 is also withdrawn in direction 690 away from the stent 652 and outward from the patient. However, the stent 652 and bone fusion material 682 are left in vivo to bond with the transverse processes 404, as shown in FIG. 44.

Figure 45:
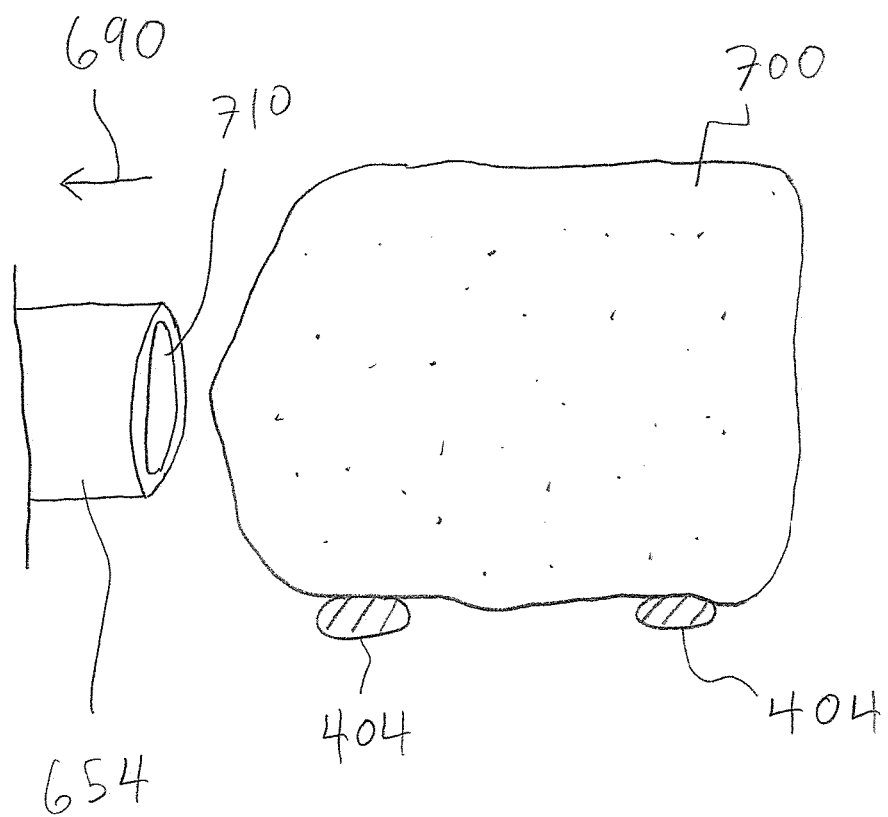
FIG. 45 is a view similar to FIG. 44 except that the stent has been withdrawn with the support tube leaving only the bone fusion material in contact with the transverse processes.

In an alternative approach shown in FIG. 45, the stent 652 remains connected 657 to the support tube 656 and both the support tube 656 and stent 652 are withdrawn through the cannula 710 of the catheter 654. This leaves the bone fusion material 682 in the patient without the stent 652. The bone fusion material 682 may then bond with the transverse processes 404.

In yet another approach, the stent 652 includes an inner portion made of a bioabsorbable polymer material and an outer portion made of stainless steel. The outer portion is fixed to the support tube 656 while the inner portion is held within an inner compartment of the outer portion due to the collapsed, insertion configuration of the outer portion. Once the stent 656 has been positioned near one or more bones, the inner and outer portions are shifted to an expanded configuration and bone fusion material can be advanced into a compartment of the stent inner portion in a manner similar to the approach of FIGS. 42 and 43. Next, the outer portion of the stent 656, which remains connected to the support tube 656, is withdrawn through the cannula 710 of the catheter 654. The inner portion of the stent 656 filled with bone fusion material is thereby left in the patient and is absorbed.

Figure 46:
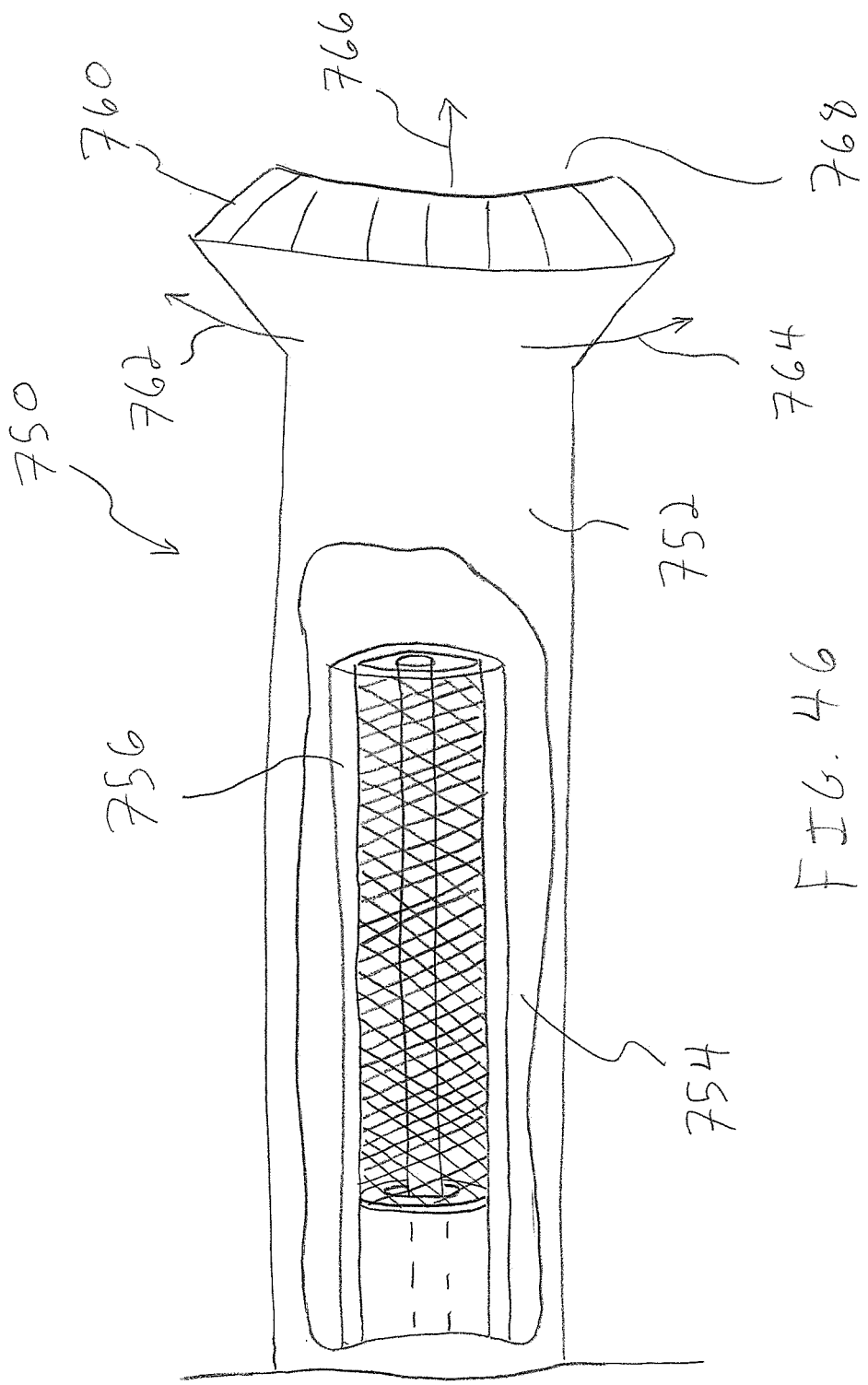
FIG. 46 is a perspective view of an instrument with a portion of a shaft of the instrument removed to show a stent delivery instrument similar to the instrument of FIG. 40 housed within the shaft of the instrument.

With reference to FIG. 46, an instrument 750 is shown having a cannulated burr 752 with an inner bore 754 that receives an expansion device delivery instrument 756 similar to the instrument 650 discussed above. The instrument 750 includes a bone preparation portion 760 that can be advanced into contact with bone and rotated in opposite rotary directions 762, 764 to prepare the surface of a bone. Once the surface of the bone has been treated, the burr 752 may be partially withdrawn and/or the expansion device delivery instrument 756 advanced forward from the burr 752 in direction 766 outward from an opening 768 of the burr 752. The expansion device delivery instrument 756 may then be maneuvered into a desired position near the bone and used to deliver an expansion device, as discussed above with respect to instrument 650.

Figure 47:
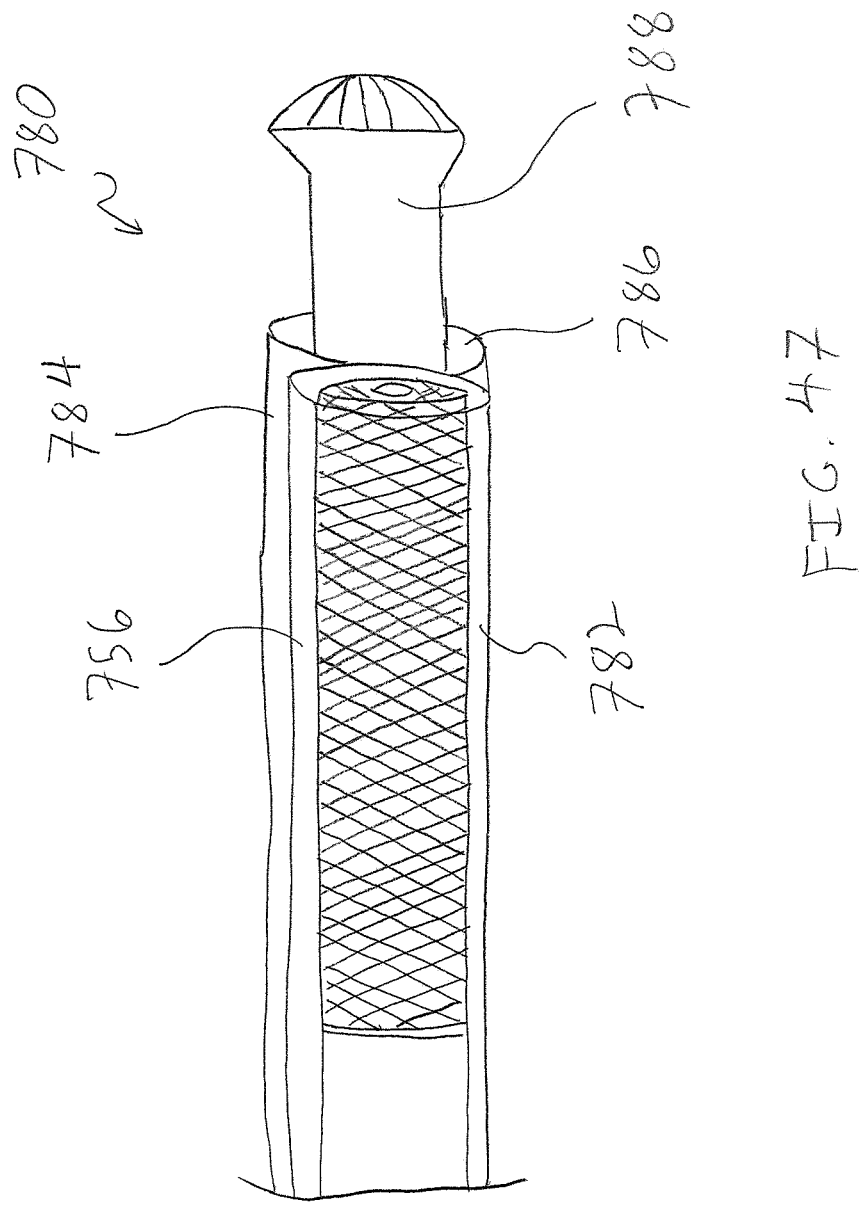
FIG. 47 is a perspective view of another instrument including a side-by-side stent delivery device and a cannula through which a burr is advanced.

With reference to FIG. 47, another instrument 780 is shown that is similar to instrument 750 such that differences between the two will be highlighted. The instrument 750 includes the expansion delivery device instrument 756 within a catheter 782. The instrument 780 also has a lumen 784 positioned laterally relative to the catheter 782. The lumen 784 has an opening 786 sized to permit a burr 788 to be advanced through the lumen 784 and into engagement with a bone.

Figure 48:
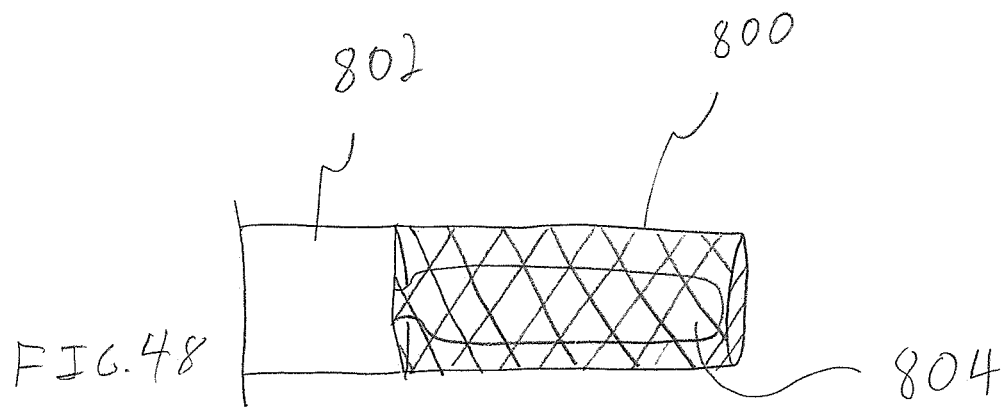
FIG. 48 is a schematic view of a stent delivery instrument including a stent with an internal compartment and a balloon received in the internal compartment.
Figure 49:
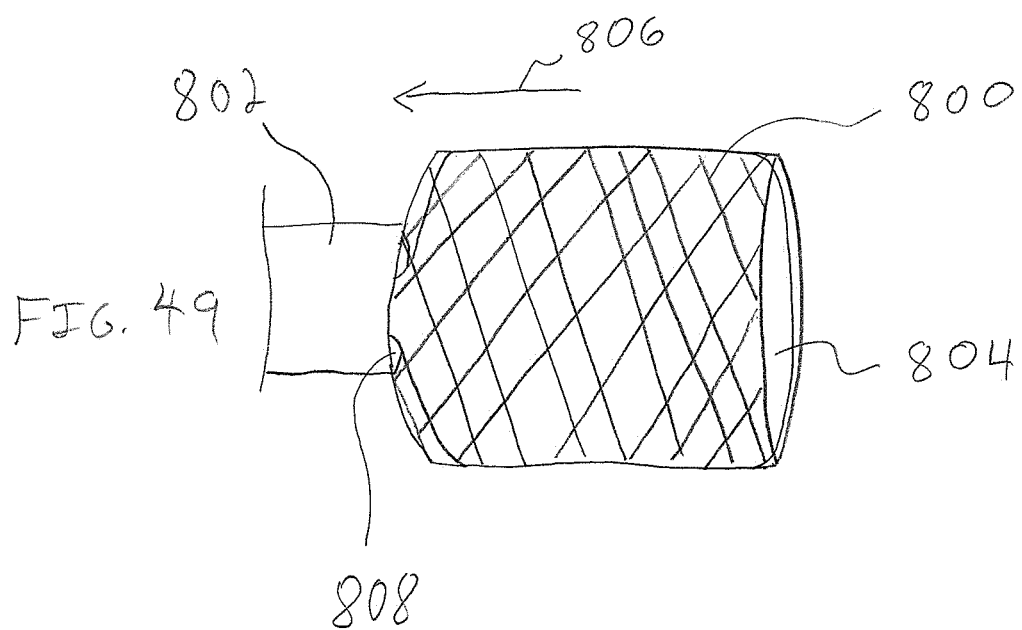
FIG. 49 is a view similar to FIG. 48 showing the balloon expanded which shifts the stent to an expanded configuration.
Figure 50:
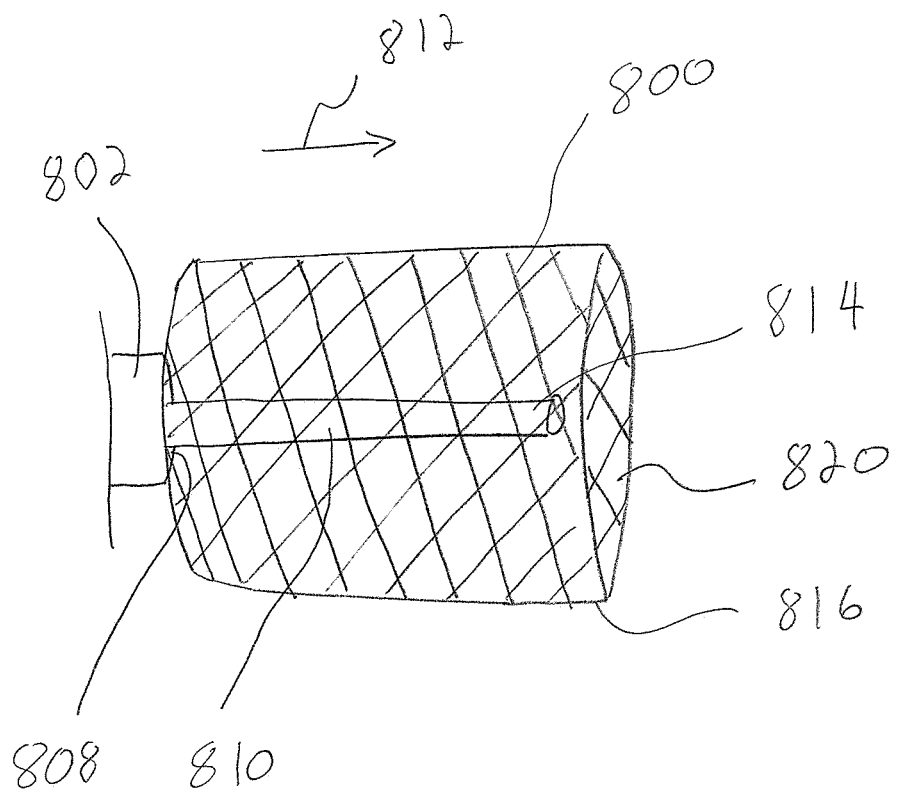
FIG. 50 is a view similar to FIG. 48 showing the balloon removed from the stent compartment and a bone fusion substance delivery tube advanced into the stent compartment.

With reference to FIGS. 48-50, another expansion device is shown having a stent 800 connected to a support tube 802 and an expansion mechanism, such as a balloon 804. The stent 800 is advanced into position near one or more bones and the balloon 804 is expanded to shift the stent 800 to an expanded configuration. In one approach, the balloon 804 is inflated using a compressor located outside of the patient and in fluid communication with the balloon 804 along the support tube 802. The balloon 804 may then be deflated and withdrawn in direction 806 through a cannula 808 of the support 802. The stent 800 retains its expanded form after removal of the balloon 804, such as by interlocking members of the stent 200.

With reference to FIG. 50, a bone fusion material delivery tube 810 is then advanced distally in direction 812 out from the cannula 808 of the support 802. The delivery tube 810 has a distal end 814 positioned near a distal end 816 of the stent 800. Bone fusion material may then be discharged from the graft delivery tube 810 as the graft delivery tube 810 is retracted to fill the stent cavity 820 as discussed above with respect to FIGS. 42 and 43.

Figure 51:
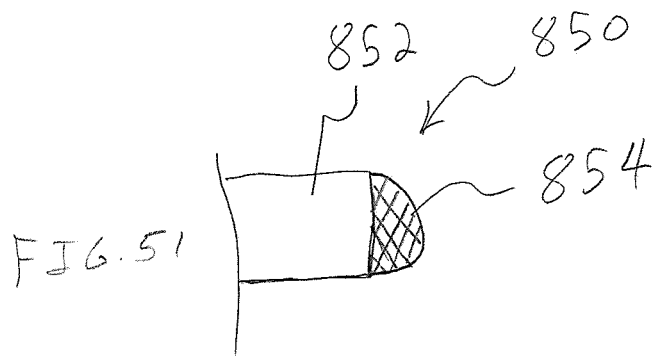
FIG. 51 is a schematic view of a mesh bag carried by a delivery instrument.
Figure 52:
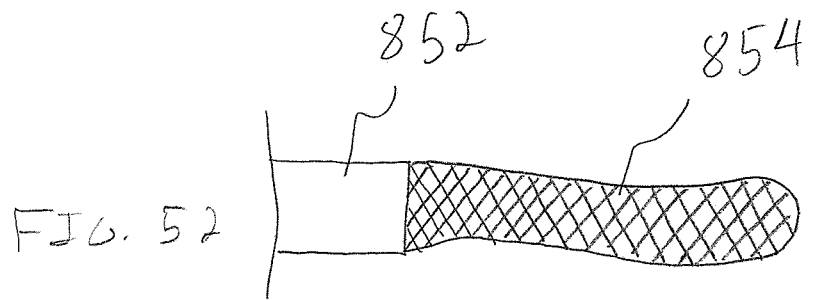
FIG. 52 is a view similar to FIG. 51 showing a bone fusion substance being injected into the mesh bag.
Figure 53:
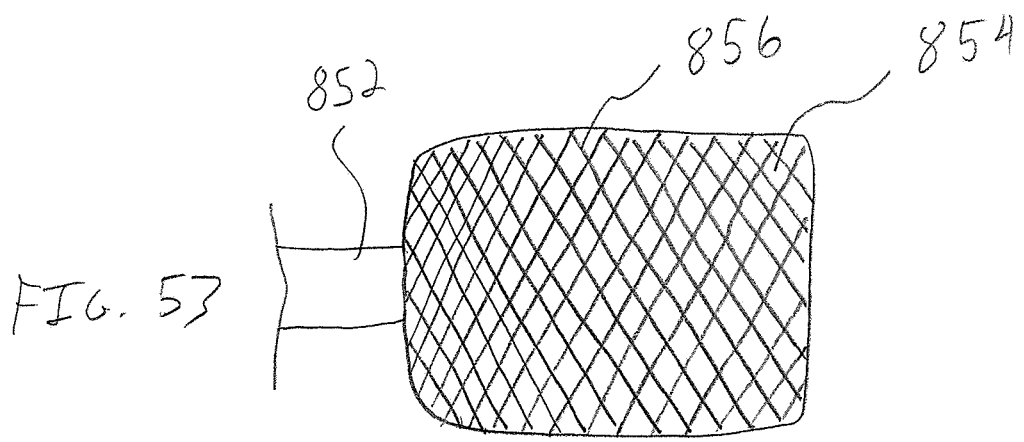
FIG. 53 is a view similar to FIG. 52 showing bone fusion substance having been injected into the mesh bag to fully expand the mesh bag.

With reference to FIGS. 51-53, another expansion device 850 is shown that includes a support 852 and a mesh bag 854. The mesh bag 854 is initially in a retracted position as the expansion device 850 is maneuvered into position near one or more bones.

Next, the mesh bag 854 is advanced outward from the support 852. The bag 854 may be advanced into a cavity formed using the tissue mover 250, as discussed above with respect to FIG. 30. Bone fusion material 856 is then injected into the mesh bag 854 which expands the bag 854. The expansion of the mesh bag 854 produced by injection of the graft 856 may apply a distracting force can separate tissues surrounding the mesh bag 854.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A method of applying bone fusion material to a plurality of bones, the method comprising:
   separating tissues adjacent the bones to form a cavity extending between the bones;
   positioning a guide instrument having a shaft and a tip extending transverse to the shaft so that the tip extends along the cavity;
   advancing a bone fusion material delivery instrument along the shaft of the guide instrument and toward the cavity;
   directing bone fusion material from an opening of the bone fusion material delivery instrument into the cavity and along the tip of the guide instrument; and
   using the tip of the guide instrument and tissues about the cavity to guide the bone fusion material along the cavity.

2. The method of claim 1 wherein advancing the bone fusion material delivery instrument along the shaft of the guide instrument includes advancing the bone fusion material delivery instrument to position the opening of the bone fusion material delivery instrument adjacent the tip of the guide instrument.

3. The method of claim 2 wherein directing the bone fusion material from the opening of the bone fusion material delivery instrument includes directing the bone fusion material from the opening of the bone fusion material delivery instrument positioned adjacent the tip of the guide instrument.

4. The method of claim 1 wherein the shaft and the tip of the guide instrument each extend along a respective axis and positioning the guide instrument includes positioning the guide instrument so that the axes of the shaft and tip of the guide instrument extend substantially perpendicular to each other.

5. The method of claim 1 wherein directing the bone fusion material from the opening of the bone fusion material delivery instrument includes shifting a plunger of the bone fusion material delivery instrument longitudinally within a bore of the bone fusion material delivery instrument and directing the bone fusion material laterally from the opening of the bone fusion material delivery instrument.

6. The method of claim 1 wherein using the tip of the guide instrument and tissues about the cavity to guide the bone fusion material along the cavity includes manipulating a handle of the guide instrument disposed outside of the tissues while the tip of the guide instrument extends along the cavity.

7. The method of claim 1 further comprising making an incision adjacent one of the bones and positioning the guide instrument includes inserting the tip of the guide instrument into the incision and advancing the bone fusion material delivery instrument includes advancing a portion of the bone fusion material delivery instrument into the incision.

8. The method of claim 1 wherein advancing the bone fusion material delivery instrument along the shaft includes advancing a portion of the bone fusion material delivery instrument along a channel of the shaft.

9. The method of claim 1 wherein the bones are transverse processes of vertebrae and separating the tissues includes sweeping tissues away from a posterolateral gutter adjacent the transverse processes.

10. The method of claim 1 wherein directing the bone fusion material from the opening of the bone fusion material delivery instrument includes directing the bone fusion material into a first end portion of the cavity and along the cavity in a first direction; and
    directing additional bone fusion material from the opening of the bone fusion material delivery instrument into a second end portion of the cavity and along the cavity in a second direction opposite to the first direction.

11. A method of applying bone fusion material to transverse processes of vertebrae, the method comprising:
    separating tissues adjacent first and second transverse processes to form a cavity extending between the first and second transverse processes;
    positioning a tip of a guide instrument in the cavity so that the tip extends between the first transverse process and the second transverse process;
    advancing a bone fusion material delivery instrument along the guide instrument to position an opening of the bone fusion material delivery instrument adjacent the tip of the guide instrument and the first transverse process; and
    directing bone fusion material from the opening of the bone fusion material delivery instrument along the tip of the guide instrument and toward the second transverse process within the cavity.

12. The method of claim 11 wherein advancing the bone fusion material delivery instrument along the guide instrument includes advancing the bone fusion material delivery instrument in a first direction and directing the bone fusion material from the opening of the bone fusion material delivery instrument includes directing the bone fusion material in a second direction substantially perpendicular to the first direction.

13. The method of claim 11 wherein directing the bone fusion material from the opening of the bone fusion material delivery instrument includes shifting a plunger of the bone fusion material delivery instrument longitudinally within a bore of the bone fusion material delivery instrument and directing the bone fusion material laterally from the opening of the bone fusion material delivery instrument.

14. The method of claim 11 further comprising manipulating a handle of the guide instrument outside of the tissues to keep the tissues separated while the tip of the guide instrument is in the cavity.

15. The method of claim 11 wherein advancing the bone fusion material delivery instrument along the guide instrument includes advancing a portion of the bone fusion material delivery instrument that includes the opening along a channel of the guide instrument.

16. The method of claim 11 further comprising making an incision adjacent the first transverse process and positioning the tip of the guide instrument in the cavity includes inserting the tip of the guide instrument into the incision and advancing the bone fusion delivery instrument along the guide instrument includes advancing a portion of the bone fusion material delivery instrument into the incision.

17. The method of claim 11 wherein directing the bone fusion material from the opening of the bone fusion material delivery instrument includes directing the bone fusion material into a first end portion of the cavity and along the cavity in a first direction; and
  directing additional bone fusion material from the opening of the bone fusion material delivery instrument into a second end portion of the cavity and along the cavity in a second direction opposite to the first direction.

18. A method comprising:
  providing a guide instrument having a shaft and a tip extending transverse to the shaft, the tip of the guide instrument being configured to be positioned in a cavity extending between bones; and
  providing a bone fusion material delivery instrument having an internal volume for receiving bone fusion material and a distal end portion configured to be advanced along the shaft of the guide instrument and into the cavity, the distal end portion having an opening through which the bone fusion material may be directed into the cavity and along the tip of the guide instrument.

19. The method of claim 18 wherein providing the guide instrument includes providing the guide instrument having the shaft and tip thereof extending along respective axes that are substantially perpendicular to each other.

20. The method of claim 18 wherein providing the bone fusion material delivery instrument includes providing the bone fusion material delivery instrument having an actuator that is longitudinally shiftable to cause the bone fusion material to discharge laterally through the opening of the bone fusion material delivery instrument.

21. The method of claim 18 wherein providing the guide instrument includes providing the guide instrument having a channel and providing the bone fusion delivery instrument includes providing the bone fusion delivery instrument having the distal end portion configured to fit at least partially within the channel of the guide instrument.

* * * * *